United States Patent [19]
Zoller et al.

[11] Patent Number: 5,981,492
[45] Date of Patent: *Nov. 9, 1999

[54] SUBSTITUTED 5-MEMBERED RING HETEROCYCLES, THEIR PREPARATION AND THEIR USE

[75] Inventors: Gerhard Zoller, Schoneck; Otmar Klingler, Rodgau; Bernd Jablonka, Oberursel; Melitta Just, Langen; Gerhard Breipohl, Frankfurt am Main; Jochen Knolle, Kriftel; Wolfgang Konig, Stallwang; Hans-Ulrich Stilz, Frankfurt am Main, all of Germany

[73] Assignee: Hoechst Aktiengesellschaft, Frankfurt am Main, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/640,895

[22] PCT Filed: Oct. 24, 1994

[86] PCT No.: PCT/EP94/03491

§ 371 Date: Jul. 19, 1996

§ 102(e) Date: Jul. 19, 1996

[87] PCT Pub. No.: WO95/14008

PCT Pub. Date: May 26, 1995

[30] Foreign Application Priority Data

Nov. 15, 1993 [DE] Germany .............................. 43 38 944
Aug. 8, 1994 [DE] Germany .............................. 44 27 979

[51] Int. Cl.$^6$ ........................ A61K 37/02; A61K 31/415; C07D 233/76; C07D 233/96; C07D 223/72; C07D 263/44

[52] U.S. Cl. ................................ 514/20; 514/18; 514/19; 514/385; 514/389; 514/391; 514/398; 548/318.1; 548/318.5; 548/319.1

[58] Field of Search ............................... 548/318.1, 318.5, 548/319.5; 514/389, 391, 398, 385, 18, 19, 20

[56] References Cited

U.S. PATENT DOCUMENTS

| | | | |
|---|---|---|---|
| 3,300,510 | 1/1967 | Auburn et al. | 548/319.5 |
| 5,389,614 | 2/1995 | Konig et al. | 514/18 |
| 5,397,796 | 3/1995 | Zoller et al. | 514/389 |
| 5,424,293 | 6/1995 | Zoller et al. | 514/20 |

FOREIGN PATENT DOCUMENTS

| | | | |
|---|---|---|---|
| B-73653/91 | 10/1991 | Australia | 514/389 |
| 6352 | 1/1980 | European Pat. Off. | 514/18 |
| 0449079 | 10/1991 | European Pat. Off. | 548/319.5 |
| 512 831 | 11/1992 | European Pat. Off. | 514/20 |
| 0530505 | 3/1993 | European Pat. Off. | 548/319.5 |
| 0566919 | 10/1993 | European Pat. Off. | 548/319.5 |
| 2714655 | 10/1978 | Germany | 548/319.5 |
| 2032419 | 5/1980 | United Kingdom | 514/389 |
| WOA 93/18057 | 9/1993 | WIPO | 514/14 |
| WOA 94/17034 | 8/1994 | WIPO | 514/20 |
| WOA 94/21607 | 9/1994 | WIPO | 514/389 |

*Primary Examiner*—Floyd D. Higel
*Attorney, Agent, or Firm*—Perman & Green, LLP

[57] ABSTRACT

The present invention pertains to 5-ring heterocycles of general formula (I), wherein W, Y, Z, B, D, E and R as well as b, c, d, e, f, g, and h are as indicated in the description; to methods for preparing them, and to their use as inhibitors of platelet aggregation, metastasizing of carcinomatous cells and the attachment of osteoclasts to the bone surface.

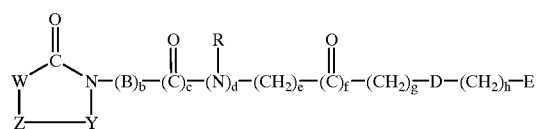

(I)

29 Claims, No Drawings

SUBSTITUTED 5-MEMBERED RING HETEROCYCLES, THEIR PREPARATION AND THEIR USE

The present invention relates to substituted 5-membered ring heterocycles, their preparation and their use as medicines, in particular as inhibitors of blood platelet aggregation.

EP-A-449 079, EP-A-530 505, EP-A-566 919 and WO-A-93/18057 describe hydantoin derivatives which exhibit thrombocyte aggregation-inhibiting effects. EP-A 512 831 mentions pyrrolidone derivatives which prevent the binding of fibrinogen to blood platelets and hence aggregation of the platelets. Further investigations demonstrated that the compounds of the present invention are also strong inhibitors of blood platelet aggregation.

The present invention relates to 5-membered ring heterocycles of the general formula I,

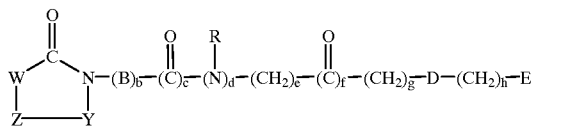

in which

W represents $R^1$—A—$C(R^{13})$ or $R^1$—A—CH=C;

Y represents a carbonyl group, a thiocarbonyl group or a methylene group;

Z represents $N(R^0)$, oxygen, sulphur or a methylene group;

A denotes a divalent radical from the group $(C_1$–$C_6)$-alkylene, $(C_3$–$C_7)$-cycloalkylene, phenylene, phenylene-$(C_1$–$C_6)$-alkyl, $(C_1$–$C_6)$-alkylene-phenyl or phenylene-$(C_2$–$C_6)$-alkenyl, or a divalent radical of a 5-membered or 6-membered saturated or unsaturated ring which can contain 1 or 2 nitrogen atoms and can be substituted once or twice by $(C_1$–$C_6)$-alkyl or doubly bonded oxygen or sulphur;

B denotes a divalent radical from the group $(C_1$–$C_6)$-alkylene, $(C_2$–$C_6)$-alkenylene, phenylene, phenylene-$(C_1$–$C_3)$-alkyl or $(C_1$–$C_3)$-alkylene-phenyl;

D represents $C(R^2)(R^3)$, $N(R^3)$ or $CH=C(R^3)$;

E denotes tetrazolyl, $(R^8O)_2P(O)$, $HOS(O)_2$, $R^9NHS(O)_2$ or $R^{10}CO$;

R and $R^0$ denote, independently of each other, hydrogen, $(C_1$–$C_8)$-alkyl, $(C_3$–$C_8)$-cycloalkyl, optionally substituted $(C_6$–$C_{14})$-aryl, or $(C_6$–$C_{14})$-aryl-$(C_1$–$C_8)$-alkyl which is optionally substituted in the aryl radical;

$R^1$ represents X—NH—C(=NH)—$(CH_2)_9$ or $X^1$—NH—$(CH_2)_p$, where p can represent an integer from 0 to 3;

X denotes hydrogen, $(C_1$–$C_6)$-alkyl, $(C_1$–$C_6)$-alkylcarbonyl, $(C_1$–$C_6)$-alkoxycarbonyl, $(C_1$–$C_{18})$-alkylcarbonyloxy-$(C_1$–$C_6)$-alkoxycarbonyl, optionally substituted $(C_6$–$C_{14})$-aryloxycarbonyl, $(C_6$–$C_{14})$-aryl-$(C_1$–$C_6)$-alkoxycarbonyl which can also be substituted in the aryl radical, $(R^8O)_2P(O)$, cyano, hydroxyl, $(C_1$–$C_6)$-alkoxy, $(C_6$–$C_{14})$-aryl-$(C_1$–$C_6)$-alkoxy which can also be substituted in the aryl radical, or amino;

$X^1$ has one of the meanings of X or denotes R' —NH—C(=N—R"), where R' and R", independently of each other, have the meanings of X;

$R^2$ denotes hydrogen, $(C_1$–$C_8)$-alkyl, optionally substituted $(C_6$–$C_{14})$-aryl, $(C_6$–$C_{14})$-aryl-$(C_1$–$C_8)$-alkyl which is optionally substituted in the aryl radical, or $(C_3$–$C_8)$-cycloalkyl;

$R^3$ denotes hydrogen, $(C_1$–$C_8)$-alkyl, optionally substituted $(C_6$–$C_{14})$-aryl, $(C_6$–$C_{14})$-aryl-$(C_1$–$C_8)$-alkyl which is optionally substituted in the aryl radical, $(C_3$–$C_8)$-cycloalkyl, $(C_2$–$C_8)$-alkenyl, $(C_2$–$C_8)$-alkynyl, $(C_2$–$C_8)$-alkenylcarbonyl, $(C_2$–$C_8)$-alkynlcarbonyl, pyridyl, $R^{11}NH$, $R^4CO$, $COOR^4$, $CON(CH_3)R^{14}$, $CONHR^{14}$, $CSNHR^{14}$, $COOR^{15}$, $CON(CH_3)R^{15}$ or $CONHR^{15}$;

$R^4$ denotes hydrogen or $(C_1$–$C_{28})$-alkyl which can optionally be substituted once or more than once by identical or different radicals $R^{4'}$;

$R^{4'}$ denotes hydroxyl, hydroxycarbonyl, aminocarbonyl, mono- or di-$((C_1$–$C_{18})$-alkyl)-aminocarbonyl, amino-$(C_2$–$C_{18})$-alkylamino-carbonyl, amino-$(C_1$–$C_3)$-alkylphenyl-$(C_1$–$C_3)$-alkylamino-carbonyl, $(C_1$–$C_{18})$-alkylcarbonylamino-$(C_1$–$C_3)$-alkylphenyl-$(C_1$–$C_{18})$-alkylaminocarbonyl, $(C_1$–$C_{18})$-alkylcarbonylamino-$(C_2$–$C_{18})$-alkylaminocarbonyl, $(C_6$–$C_{14})$-aryl-$(C_1$–$C_8)$-alkoxy-carbonyl which can also be substituted in the aryl radical, amino, mercapto, $(C_1$–$C_{18})$-alkoxy, $(C_1$–$C_{18})$-alkoxycarbonyl, optionally substituted $(C_3$–$C_8)$-cycloalkyl, halogen, nitro, trifluoromethyl or the radical $R^5$;

$R^5$ denotes optionally substituted $(C_6$–$C_{14})$-aryl, $(C_6$–$C_{14})$-aryl-$(C_1$–$C_8)$-alkyl which is optionally substituted in the aryl radical, a monocyclic or bicyclic 5- to 12-membered heterocyclic ring which can be aromatic, partially hydrogenated or completely hydrogenated and which can contain one, two or three identical or different heteroatoms from the group nitrogen, oxygen and sulphur, a radical $R^6$ or a radical $R^6CO$—, where the aryl radical and, independently thereof, the heterocycle radical can be substituted once or more than once by identical or different radicals from the group $(C_1$–$C_{18})$-alkyl, $(C_1$–$C_{18})$-alkoxy, halogen, nitro, amino or trifluoromethyl;

$R^6$ represents $R^7R^8N$, $R^7O$ or $R^7S$, or denotes an amino acid side chain, a natural or unnatural amino acid radical, imino acid radical, optionally N—$(C_1$–$C_8)$-alkylated or N—$((C_6$–$C_{14})$-aryl-$(C_1$–$C_8)$-alkylated) azaamino acid radical or a dipeptide radical which can also be substituted in the aryl radical and/or in which the peptide bond can be reduced to —NH—$CH_2$—, and also the esters and amides thereof, where hydrogen or hydroxymethyl can optionally stand in place of free functional groups and/or where free functional groups can be protected by protective groups which are customary in peptide chemistry;

$R^7$ denotes hydrogen, $(C_1$–$C_{18})$-alkyl, $(C_6$–$C_{14})$-aryl-$(C_1$–$C_8)$-alkyl, $(C_1$–$C_{18})$-alkylcarbonyl, $(C_1$–$C_{18})$-alkoxycarbonyl, $(C_6$–$C_{14})$-arylcarbonyl, $(C_6$–$C_{14})$-aryl-$(C_1$–$C_8)$-alkylcarbonyl or $(C_6$–$C_{14})$-aryl-$(C_1$–$C_{18})$-alkoxycarbonyl, where the alkyl groups can optionally be substituted by an amino group and/or where the aryl radicals can be substituted once or more than once, preferably once, by identical or different radicals from the group $(C_1$–$C_8)$-alkyl, $(C_1$–$C_8)$-alkoxy, halogen, nitro, amino and trifluoromethyl, a natural or unnatural amino acid radical, imino acid radical, optionally N—$(C_1$–$C_8)$-alkylated or N—$((C_6$–$C_{14})$-aryl-$(C_1$–$C_8)$-alkylated) azaamino acid radical or a dipeptide radical which can also be substituted in the aryl radical and/or in which the peptide bond can be reduced to —NH—CH$_2$—;

$R^8$ denotes hydrogen, (C$_1$–C$_{18}$)-alkyl, optionally substituted (C$_6$–C$_{14}$)-aryl or (C$_6$–C$_{14}$)-aryl-(C$_1$–C$_8$)-alkyl which can also be substituted in the aryl radical;

$R^9$ denotes hydrogen, aminocarbonyl, (C$_1$–C$_{18}$)-alkylaminocarbonyl, (C$_3$–C$_8$)-cycloalkylaminocarbonyl, optionally substituted (C$_6$–C$_{14}$)-arylaminocarbonyl, (C$_1$–C$_{18}$)-alkyl, optionally substituted (C$_6$–C$_{14}$)-aryl, or (C$_3$–C$_8$)-cycloalkyl;

$R^{10}$ denotes hydroxyl, (C$_1$–C$_{18}$)-alkoxy, (C$_6$–C$_{14}$)-aryl-(C$_1$–C$_8$)-alkoxy which can also be substituted in the aryl radical, optionally substituted (C$_6$–C$_{14}$)-aryloxy, amino or mono- or di-((C$_1$–C$_{18}$)-alkyl)-amino;

$R^{11}$ denotes hydrogen, (C$_1$–C$_{18}$)-alkyl, $R^{12}$CO, optionally substituted (C$_6$–C$_{14}$)-aryl-S(O)$_2$, (C$_1$–C$_{18}$)-alkyl-S(O)$_2$, (C$_6$–C$_{14}$)-aryl-(C$_1$–C$_8$)-alkyl which is optionally substituted in the aryl radical, or $R^9$NHS(O)$_2$;

$R^{12}$ denotes hydrogen, (C$_1$–C$_{18}$)-alkyl, (C$_2$–C$_8$)-alkenyl, (C$_2$–C$_8$)-alkynyl, optionally substituted (C$_6$–C$_{14}$)-aryl, (C$_1$–C$_{18}$)-alkoxy, (C$_6$–C$_{14}$)-aryl-(C$_1$–C$_8$)-alkoxy which can also be substituted in the aryl radical, optionally substituted (C$_6$–C$_{14}$)-aryloxy, amino or mono- or di-((C$_1$–C$_{18}$)-alkyl)-amino;

$R^{13}$ denotes hydrogen, (C$_1$–C$_6$)-alkyl, (C$_6$–C$_{14}$)-aryl-(C$_1$–C$_8$)-alkyl which is optionally substituted in the aryl radical, or (C$_3$–C$_8$)-cycloalkyl;

$R^{14}$ denotes hydrogen or (C$_1$–C$_{28}$)-alkyl which can optionally be substituted once or more than once by identical or different radicals from the group hydroxyl, hydroxycarbonyl, amino-carbonyl, mono- or di-((C$_1$–C$_{18}$)-alkyl)-aminocarbonyl, amino-(C$_2$–C$_{18}$)-alkylaminocarbonyl, amino-(C$_1$–C$_3$)-alkylphenyl-(C$_1$–C$_3$)-alkylaminocarbonyl, (C$_1$–C$_{18}$)-alkylcarbonylamino-(C$_1$–C$_3$)-alkylphenyl-(C$_1$–C$_3$)-alkylaminocarbonyl, (C$_1$–C$_{18}$)-alkylcarbonyl-amino-(C$_2$–C$_{18}$)-alkylaminocarbonyl, (C$_6$–C$_{14}$)-aryl-(C$_1$–C$_8$)-alkoxycarbonyl which can also be substituted in the aryl radical, amino, mercapto, (C$_1$–C$_{18}$)-alkoxy, (C$_1$–C$_{18}$)-alkoxycarbonyl, optionally substituted (C$_3$–C$_8$)-cycloalkyl, HOS(O)$_2$—(C$_1$–C$_3$)-alkyl, $R^9$NHS(O)$_2$—(C$_1$–C$_3$)-alkyl, (R$^8$O)$_2$P(O)—(C$_1$–C$_3$)-alkyl, tetrazolyl-(C$_1$–C$_3$)-alkyl, halogen, nitro, trifluoromethyl and $R^5$;

$R^{15}$ represents $R^{16}$-(C$_1$–C$_6$)-alkyl or represents $R^{16}$;

$R^{16}$ represents a 6- to 24-membered bicyclic or tricyclic radical which is saturated or partially unsaturated and which can also contain one to four identical or different heteroatoms from the group nitrogen, oxygen and sulphur, and which can also be substituted by one or more identical or different substituents from the group (C$_1$–C$_4$)-alkyl and oxo;

b, c, d and f, independently of each other, can represent 0 or 1, but cannot all simultaneously be 0;

e, g and h, independently of each other, can represent integers from 0 to 6;

where, however, when, at the same time, W represents $R^1$—A—CH or $R^1$—A—CH=C, D represents N(R$^3$) and c, d and f represent 0, $R^3$ cannot then represent COOR$^a$ or CONHR$^b$, where R$^a$ represents methyl which is substituted by a 9-fluorenyl radical and R$^b$ represents methyl which is substituted by a phenyl radical and a methoxy-carbonyl group;

and where, when, at the same time, W represents $R^1$—A—CH or $R^1$—A—CH=C, D represents C(R$^2$) (R$^3$), R$^2$ represents hydrogen or phenyl, and e, f and g represent 0, R$^3$ cannot then represent hydrogen, COOR$^4$, CONHR$^4$ or CON(CH$_3$)R$^4$ or, when Z also at the same time represents a methylene group, cannot represent CONHR$^c$, where R$^4$ represents hydrogen, unsubstituted (C$_1$–C$_{28}$)-alkyl or (C$_1$–C$_{28}$)-alkyl which is exclusively substituted once or more than once by identical or different R$^{4'}$radicals, and R$^c$ represents methyl which is substituted by a phenyl radical and an aminocarbonyl-aminosulphonyl group;

and the physiologically tolerated salts thereof.

Cycloalkyl radicals are, in particular, cyclopropyl, cyclobutyl, cyclopentyl, cyclohexyl, cycloheptyl and cyclooctyl, which, however, can also be substituted by, for example, (C$_1$–C$_4$)-alkyl. Examples of substituted cycloalkyl radicals are 4-methyl-cyclohexyl and 2,3-dimethylcyclopentyl. This also applies in an analogous manner for cycloalkylene radicals.

Alkyl radicals can be straight-chain or branched. This also applies when they carry substituents or appear as substituents of other radicals, for example in alkoxy radicals, alkoxycarbonyl radicals or aralkyl radicals. This applies in a corresponding manner for alkylene radicals. Examples of suitable C$_1$–C$_{28}$-alkyl radicals are: methyl, ethyl, propyl, butyl, pentyl, hexyl, heptyl, octyl, decyl, undecyl, dodecyl, tridecyl, pentadecyl, hexadecyl, heptadecyl, nonadecyl, eicosyl, docosyl, tricosyl, pentacosyl, hexacosyl, heptacosyl, octacosyl, isopropyl, isopentyl, neopentyl, isohexyl, 3-methylpentyl, 2,3,5-trimethyl-hexyl, sec-butyl, tert-butyl and tert-pentyl. Preferred alkyl radicals are methyl, ethyl, propyl, isopropyl, butyl, isobutyl, sec-butyl and tert-butyl. Examples of alkylene radicals are methylene, ethylene, trimethylene, tetramethylene, pentamethylene and hexamethylene.

Alkenyl radicals and alkenylene radicals, and also alkynyl radicals, can also be straight-chain and branched. Examples of alkenyl radicals are vinyl, 1-propenyl, allyl, butenyl and 3-methyl-2-butenyl, of alkenylene radicals, vinylene or propenylene, and of alkynyl radicals, ethynyl, 1-propynyl or propargyl.

The 6- to 24-membered bicyclic and tricyclic radicals representing $R^{16}$ are obtained formally by abstracting a hydrogen atom from bicycles or tricycles, respectively. While the underlying bicycles and tricycles can contain only carbon atoms as ring members, and can thus be bicycloalkanes and tricycloalkanes, they can also contain 1 to 4 identical or different heteroatoms from the group nitrogen, oxygen and sulphur and can thus be aza-, oxa- and thia-bicycloalkanes and aza-, oxa- and thia-tricycloalkanes. If heteroatoms are contained, one or two heteroatoms, in particular nitrogen atoms or oxygen atoms, are then preferably contained. The heteroatoms can occupy any positions in the bicyclic or tricyclic skeleton; they can be located in the bridges or, in the case of the nitrogen atoms, also at the bridgeheads. Both the bicycloalkanes and tricycloalkanes and also their hetero analogues can be completely saturated or contain one or more double bonds; preferably, they contain one or two double bonds or are, in particular, completely saturated. Both the bicycloalkanes and tricycloalkanes and also the hetero analogues, and both the saturated and the unsaturated representatives, can be unsubstituted or be substituted in any suitable positions by one or more oxo groups and/or one or more identical or different (C$_1$–C$_4$)-alkyl groups, e.g. methyl groups or isopropyl groups, preferably methyl groups. The free bond of the bicyclic or tricyclic radical can be located in any position in the molecule; the radical can thus be bonded via a bridgehead atom or an atom in a bridge. The free bond can also be located in any stereo-chemical position, for example in an exo position or an endo position.

Examples of parent substances of bicyclic ring systems, from which a bicyclic radical representing $R^{16}$ can be derived, are norbornane (=bicyclo[2.2.1]heptane), bicyclo [2.2.2]octane and bicyclo[3.2.1]octane; examples of unsaturated or substituted systems containing heteroatoms are 7-azabicyclo[2.2.1]heptane, bicyclo[2.2.2 ]oct-5-ene and camphor (=1,7,7-trimethyl-2-oxobi-cyclo [2.2.1]heptane).

Examples of systems from which a tricyclic radical representing $R^{16}$ can be derived are twistane (=tricyclo[4.4.0.0$^{3,8}$]-decane), adamantane (=tricyclo[3.3.1.1$^{3,7}$]decane), noradamantane (=tricyclo[3.3.1.0$^{3,7}$]nonane), tricyclo [2.2.1.0$^{2,6}$]heptane, tricyclo [5.3.2.0$^{4,9}$]dodecane, tricyclo [5.4.0.0$^{2,9}$]undecane or tricyclo [5.5.1.0$^{3,11}$]tridecane.

Preferably, bicyclic or tricyclic radicals representing $R^{16}$ are derived from bridged bicycles or tricycles, that is from systems in which rings have two or more than two atoms in common. In addition to this, preference is also given to bicyclic and tricyclic radicals having from 6 to 18 ring members, particularly preferably to those having from 7 to 12 ring members.

Specific bicyclic and tricyclic radicals which are particularly preferred are the 2-norbornyl radical, both that with the free bond in the exo position and that with the free bond in the endo position, the 2-bicyclo[3.2.1]octyl radical, the 1-adamantyl radical, the 2-adamantyl radical and the 3-noradamantyl radical. Apart from this, preferred radicals are the 1-adamantyl and 2-adamantyl radicals.

Examples of ($C_6$–$C_{14}$)-aryl groups are phenyl, naphthyl, biphenylyl or fluorenyl, with 1-naphthyl, 2-naphthyl and, in particular, phenyl being preferred. Aryl radicals, in particular phenyl radicals, can be substituted once or more than once, preferably once, twice or three times, by identical or different radicals from the group ($C_1$–$C_8$)-alkyl, in particular ($C_1$–$C_4$)-alkyl, ($C_1$–$C_8$)-alkoxy, in particular ($C_1$–$C_4$)-alkoxy, halogen, nitro, amino, trifluoromethyl, hydroxyl, methylenedioxy, cyano, hydroxycarbonyl, aminocarbonyl, ($C_1$–$C_4$)-alkoxycarbonyl, phenyl, phenoxy, benzyloxy, ($R^8O)_2P(O)$, ($R^8O)_2P(O)$—O— and tetrazolyl. This applies in a corresponding manner, for example, for radicals such as aralkyl or arylcarbonyl. Aralkyl radicals are, in particular, benzyl and also 1- and 2-naphthylmethyl and 9-fluorenylmethyl, which radicals can also be substituted. Examples of substituted aralkyl radicals are halobenzyl or ($C_1$–$C_4$)-alkoxybenzyl. Examples of pyridyl are 2-pyridyl, 3-pyridyl and 4-pyridyl.

In monosubstituted phenyl radicals, the substituent can be located in the 2, the 3 or the 4 position, with the 3 and 4 positions being preferred. If phenyl is substituted twice, the substituents can be in the 1,2 positions, 1,3 positions or 1,4 positions in relation to each other. In phenyl radicals which have been substituted twice, the two substituents are preferably arranged in the 3 and 4 positions, based on the linkage site. This applies in a corresponding manner for phenylene radicals.

Phenylene-($C_1$–$C_6$)-alkyl is, in particular, phenylenemethyl and phenyleneethyl. Phenylene-($C_2$–$C_6$)-alkenyl is, in particular, phenyleneethenyl and phenylenepropenyl.

Examples of monocyclic or bicyclic 5- to 12-membered heterocyclic rings are pyrrolyl, furyl, thienyl, imidazolyl, pyrazolyl, oxazolyl, isoxazolyl, thiazolyl, isothiazolyl, tetrazolyl, pyridyl, pyrazinyl, pyrimidinyl, indolyl, isoindolyl, indazolyl, phthalazinyl, quinolyl, isoquinolyl, quinoxalinyl, quinazolinyl, cinnolinyl or a benzo-fused, cyclopenta-fused, cyclohexa-fused or cyclohepta-fused derivative of these radicals.

These heterocycles can be substituted at a nitrogen atom by ($C_1$–$C_7$)-alkyl, e.g. methyl or ethyl, phenyl or phenyl-($C_1$–$C_4$)-alkyl, e.g. benzyl, and/or at one or more carbon atoms by ($C_1$–$C_4$)-alkyl, halogen, hydroxyl, ($C_1$–$C_4$)-alkoxy, e.g. methoxy, phenyl-($C_1$–$C_4$)-alkoxy, e.g. benzyloxy, or oxo, and be aromatic or partially or completely saturated. Nitrogen heterocycles can also be present as N-oxides.

Examples of radicals of this nature are 2- or 3-pyrrolyl, phenyl-pyrrolyl, e.g. 4- or 5-phenyl-2-pyrrolyl, 2-furyl, 2-thienyl, 4-imidazolyl, methyl-imidazolyl, e.g. 1-methyl-2-, 4- or 5-imidazolyl, 1,3-thiazol-2-yl, 2-, 3- or 4-pyridyl, 2-, 3- or 4-pyridyl-N-oxide, 2-pyrazinyl, 2-, 4- or 5-pyrimidinyl, 2-, 3- or 5-indolyl, substituted 2-indolyl, e.g. 1-methyl-, 5-methyl-, 5-methoxy-, 5-benzyloxy-, 5-chloro- or 4,5-dimethyl-2-indolyl, 1-benzyl-2- or 3-indolyl, 4,5,6,7-tetrahydro-2-indolyl, cyclohepta [b]-5-pyrrolyl, 2-, 3- or 4-quinolyl, 1-, 3- or 4-isoquinolyl, 1-oxo-1,2-dihydro-3-isoquinolyl, 2-quinoxalinyl, 2-benzofuranyl, 2-benzothienyl, 2-benzoxazolyl or benzothiazolyl. Examples of partially hydrogenated or completely hydrogenated heterocyclic rings are dihydropyridinyl, pyrrolidinyl, e.g. 2-, 3- or 4-(N-methylpyrrolidinyl), piperazinyl, morpholinyl, thio-morpholinyl, tetrahydrothienyl and benzodioxolanyl.

Halogen represents fluorine, chlorine, bromine or iodine, in particular fluorine or chlorine.

Natural and unnatural amino acids can, if chiral, be present in the D form or L form. Preference D is given to α-amino acids. The following may be mentioned by way of example (cf. Houben-Weyl, Methoden der organischen Chemie (Methods of organic chemistry), Volume XV/1 and 2, Stuttgart, 1974): Aad, Abu, γAbu, ABz, 2ABz, εAca, Ach, Acp, Adpd, Ahb, Aib, βAib, Ala, βAla, ΔAla, Alg, All, Ama, Amt, Ape, Apm, Apr, Arg, Asn, Asp, Asu, Aze, Azi, Bai, Bph, Can, Cit, Cys, (Cys)$_2$, Cyta, Daad, Dab, Dadd, Dap, Dapm, Dasu, Djen, Dpa, Dtc, Fel, Gln, Glu, Gly, Guv, hAla, hArg, hCys, hGln, hGlu, His, hIle, hLeu, hLys, hMet, hPhe, hPro, hSer, hThr, hTrp, hTyr, Hyl, Hyp, 3Hyp, Ile, Ise, Iva, Kyn, Lant, Lcn, Leu, Lsg, Lys, βLys, ΔLys, Met, Mim, Min, nArg, Nle, Nva, Oly, Orn, Pan, Pec, Pen, Phe, Phg, Pic, Pro, ΔPro, Pse, Pya, Pyr, Pza, Qin, Ros, Sar, Sec, Sem, Ser, Thi, βThi, Thr, Thy, Thx, Tia, Tle, Tly, Trp, Trta, Tyr, Val, Tbg, Npg, Chg, Cha, Thia, 2,2-diphenylaminoacetic acid, 2-(p-tolyl)-2-phenylaminoacetic acid and 2-(p-chlorophenyl) aminoacetic acid.

Amino acid side chains are understood to mean side chains of natural or unnatural amino acids. Azaamino acids are natural or unnatural amino acids in which the central structural component

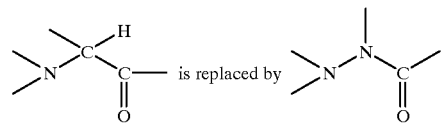

Radicals of heterocycles from the following group are particularly suitable as the radical of an imino acid: pyrrolidine-2-carboxylic acid; piperidine-2-carboxylic acid; tetrahydroisoquinoline-3-carboxylic acid; decahydroisoquinoline-3-carboxylic acid; octahydroindole-2-carboxylic acid, decahydro-quinoline-2-carboxylic acid, octahydrocyclopenta[b]pyrrole-2-carboxylic acid; 2-azabicyclo[2.2.2]octane-3-carboxylic acid; 2-azabicyclo [2.2.1]heptane-3-carboxylic acid; 2-azabicyclo[3.1.0]-hexane-3-carboxylic acid; 2-azaspiro[4.4]nonane-3- carboxylic acid; 2-azaspiro[4.5]decane-3-carboxylic acid; spiro(bicyclo-[2.2.1]heptane)-2,3-pyrrolidine-5-carboxylic acid; spiro(bicyclo-[2.2.2]octane)-2,3-pyrrolidine-5-carboxylic acid; 2-azatricyclo-[4.3.0.1$^{6,9}$]decane-3-carboxylic acid; decahydrocyclohepta [b]-pyrrole-2-carboxylic acid; decahydrocycloocta[c]pyrrole-2-carboxylic acid; octahydrocyclopenta[c]pyrrole-2-carboxylic acid; octahydroisoindole-1-carboxylic acid: 2,3,3a,4,6a-hexahydrocyclopenta [b]pyrrole-2-carboxylic acid; 2,3,3a, 4,5, 7a-hexahydroindole-2-carboxylic acid; tetrahydrothiazole-4-carboxylic acid; isoxazolidine-3-carboxylic acid; pyrazolidine-3-carboxylic acid and hydroxypyrrolidine-2-carboxylic acid; which may all optionally be substituted (see the following formulae):

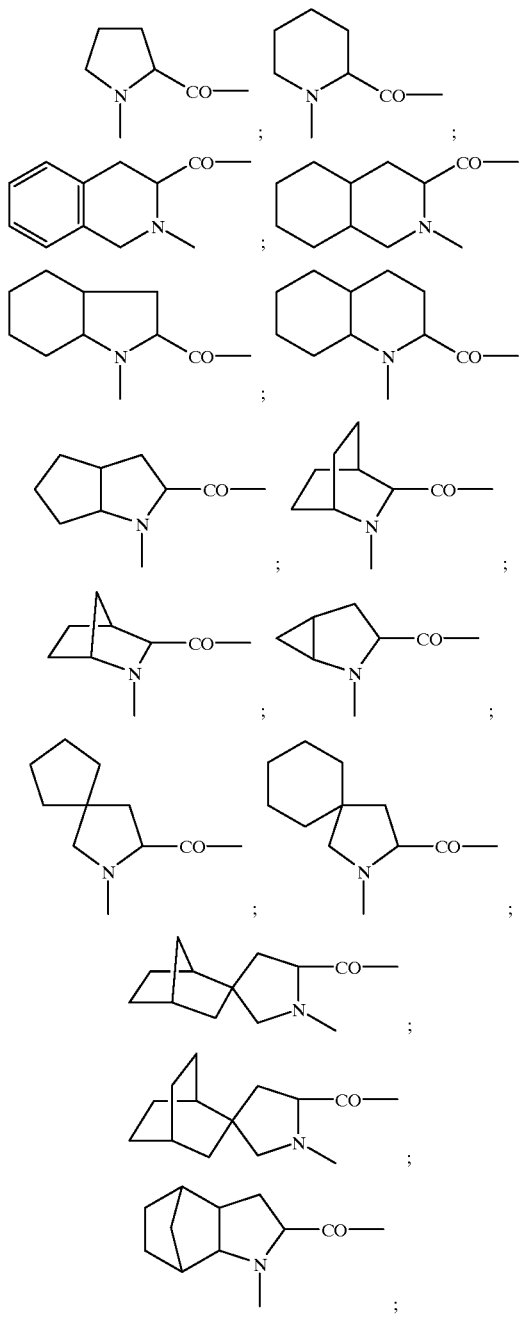
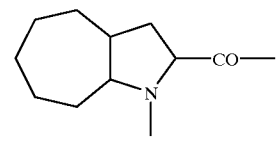
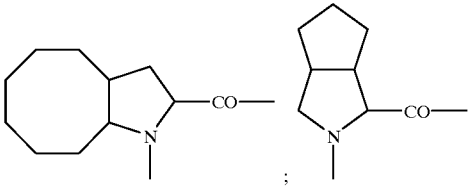
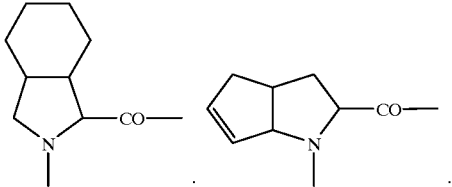
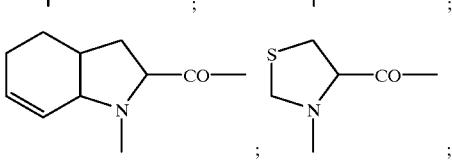
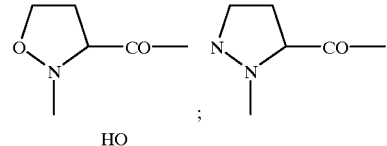

The heterocycles underlying the abovementioned radicals are known, for example, from U.S. Pat. No. 4,344,949; U.S. Pat. No. 4,374,847; U.S. Pat. No. 4,350,704; EP-A 29,488; EP-A 31,741; EP-A 46,953; EP-A 49,605; EP-A 49,658; EP-A 50,800; EP-A 51,020; EP-A 52,870; EP-A 79,022; EP-A 84,164; EP-A 89,637; EP-A 90,341; EP-A 90,362; EP-A 105,102; EP-A 109,020; EP-A 111,873; EP-A 271,865 and EP-A 344,682.

Dipeptides can contain natural or unnatural amino acids, imino acids and also azaamino acids as structural components. Furthermore, the natural or unnatural amino acids, imino acids, azaamino acids and dipeptides can also be present as esters or amides, such as, for example, methyl ester, ethyl ester, isopropyl ester, isobutyl ester, tert-butyl ester, benzyl ester, ethyl amide, semicarbazide or ω-amino-$(C_2-C_8)$-alkyl amide.

Functional groups of the amino acids, imino acids and dipeptides can be present in protected form. Suitable protective groups, such as, for example, urethane protective groups, carboxyl protective groups and side-chain protective groups, are described in Hubbuch, Kontakte (Contacts) (Merck) 1979, No. 3, pp. 14 to 23 and in Büllesbach, Kontakte (Contacts) (Merck) 1980, No. 1, pp. 23 to 35. Those which may be mentioned in particular are: Aloc, Pyoc, Fmoc, Tcboc, Z, Boc, Ddz, Bpoc, Adoc, Msc, Moc, Z(NO$_2$), Z(Hal$_n$), Bobz, Iboc, Adpoc, Mboc, Acm, tert-butyl, OBzl, ONbzl, OMbzl, Bzl, Mob, Pic, Trt.

Physiologically tolerated salts of the compounds of the general formula I are, in particular, pharmaceutically utilizable or non-toxic salts.

Such salts are formed, for example, from compounds of the general formula I which contain acidic groups, e.g. carboxyl, using alkali metals or alkaline earth metals, such as, for example, Na, K, Mg and Ca, and also using physiologically tolerated organic amines, such as, for example, triethylamine, ethanolamine or tris (2-hydroxyethyl)amine.

Compounds of the general formula I which contain basic groups, for example an amino group, an amidino group or a guanidino group, form salts with inorganic acids, such as, for example, hydrochloric acid, sulphuric acid or phosphoric acid, and with organic carboxylic or sulphonic acids, such as, for example, acetic acid, citric acid, benzoic acid, maleic acid, fumaric acid, tartaric acid, methanesulphonic acid or p-toluene-sulphonic acid.

The compounds of the general formula I according to the invention can contain optically active carbon atoms which, independently of each other, can have the R or the S configuration, and consequently be present in the form of pure enantiomers or pure diastereomers or in the form of enantiomeric mixtures or diastereomeric mixtures. Both pure enantiomers and enantiomeric mixtures and also diastereomers and diastereomeric mixtures are subject-matter of the present invention.

In addition to this, the compounds of the general formula I according to the invention can contain mobile hydrogen atoms and consequently be present in different tautomeric forms. These tautomers are also the subject-matter of the present invention.

When W represents $R^1$—A—$C(R^{13})$, A preferably represents methylene, ethylene, trimethylene, tetramethylene, cyclohexylene, phenylene, phenylenemethyl or phenyleneethenyl; when W represents $R^1$—A—CH=C, A preferably represents phenylene.

Y preferably represents a carbonyl group; Z preferably represents $N(R^0)$.

B preferably represents methylene, ethylene, trimethylene, tetramethylene, vinylene or phenylene.

D preferably represents $C(R^2)$ $(R^3)$ or $N(R^3)$.

E preferably represents $R^9NHS(O)_2$ or $R^{10}CO$.

R and $R^0$ preferably represent, independently of each other, hydrogen, $(C_1-C_6)$-alkyl or benzyl.

$R^1$ preferably represents X—NH—C(=NH), X—NH—C(=NX)—NH or X—NH—$CH_2$.

X and $X^1$ preferably represent hydrogen, $(C_1-C_6)$-alkylcarbonyl, $(C_1-C_6)$-alkoxycarbonyl, $(C_1-C_8)$-alkylcarbonyloxy-$(C_1-C_6)$-alkoxycarbonyl or $(C_6-C_{14})$-aryl-$(C_1-C_6)$-alkoxycarbonyl, with $X^1$ additionally representing $R^1$—NH—C(=NR"), where R' and R", independently of each other, have the preferred meanings of X.

$R^2$ preferably represents hydrogen or $(C_1-C_8)$-alkyl.

$R^3$ preferably represents $(C_1-C_8)$-alkyl, optionally substituted $(C_6-C_{14})$-aryl, $(C_6-C_{14})$-aryl-$(C_1-C_8)$-alkyl, $(C_3-C_8)$-cycloalkyl, $(C_2-C_8)$-alkenyl, $(C_2-C_8)$-alkynyl, pyridyl, $R^{11}NH$, $R^4CO$, $COOR^4$, $CONHR^{14}$, $CSNHR^{14}$, $COOR^{15}$ or $CONHR^{15}$.

$R^{13}$ preferably represents hydrogen and, in particular, $(C_1-C_6)$-alkyl, $(C_3-C_7)$-cycloalkyl or benzyl, where a very particularly preferred alkyl radical which $R^{13}$ represents is the methyl radical.

$R^{15}$ preferably represents $R^{16}$-$(C_1-C_3)$-alkyl or represents $R^{16}$, and particularly preferably represents $R^{16}$-$(C_1)$-alkyl or $R^{16}$. In addition to this, when $R^3$ represents $COOR^{15}$, $R^{15}$ preferably represents the exo-2-norbornyl radical, the endo-2-norbornyl radical or the 2-bicyclo[3.2.1]octyl radical, and, when $R^3$ represents $CONHR^{15}$, $R^{15}$ preferably represents the exo-2-norbornyl radical, the endo-2-norbornyl radical, the 3-noradamantyl radical, and, in particular, the 1-adamantyl radical, the 2-adamantyl radical, the 1-adamantylmethyl radical or the 2-adamantylmethyl radical.

$R^{16}$ preferably represents a 7- to 12-membered bridged bicyclic or tricyclic radical which is saturated or partially unsaturated and which also can contain one to four identical or different heteroatoms from the group nitrogen, oxygen and sulphur and which also can be substituted by one or more identical or different substituents from the group $(C_1-C_4)$-alkyl and Oxo;

b, c and d preferably represent, independently of each other, 1, e, g and h preferably represent, independently of each other, integers from 0 to 3.

Preferred compounds of the general formula I are those in which

W represents $R^1$—A—CH=C and in this A represents a phenylene radical, or W represents $R^1$—A—$C(R^{13})$ and in this A represents a divalent radical from the group methylene, ethylene, trimethylene, tetramethylene, cyclohexylene, phenylene or phenylenemethyl;

B represents a divalent radical from the group methylene, ethylene, trimethylene, tetramethylene, vinylene or phenylene;

E denotes $R^9NHS(O)_2$ or $R^{10}CO$;

R and $R^0$ denote, independently of each other, hydrogen, $(C_1-C_6)$-alkyl or benzyl;

$R^1$ represents X—NH—C(=NH), X—NH—C(=NX)—NH or X—NH—$CH_2$;

X represents hydrogen, $(C_1-C_6)$-alkylcarbonyl, $(C_1-C_6)$-alkoxycarbonyl, $(C_1-C_8)$-alkylcarbonyloxy-$(C_1-C_6)$-alkoxycarbonyl or $(C_6-C_{14})$-aryl-$(C_1-C_6)$-alkoxycarbonyl;

$R^2$ represents hydrogen or $(C_1-C_8)$-alkyl;

$R^3$ represents $(C_1-C_8)$-alkyl, optionally substituted $(C_6-C_{14})$-aryl, $(C_6-C_{14})$-aryl-$(C_1-C_8)$-alkyl, $(C_3-C_8)$-cycloalkyl, $(C_2-C_8)$-alkenyl, $(C_2-C_8)$-alkynyl, pyridyl, $R^{11}NH$, $R^4CO$, $COOR^4$, $CONHR^{14}$, $CSNHR^{14}$, $COOR^{15}$ and $CONHR^{15}$; and e, g and h, independently of each other, represent integers from 0 to 3.

Particularly preferred compounds of the general formula I are those in which $R^3$ represents optionally substituted $(C_6-C_{14})$-aryl, represents $COOR^4$, represents $R^{11}NH$ or represents $CONHR^{14}$, where —$NHR^{14}$ represents the radical of an α-amino acid, its ω-amino-$(C_2-C_8)$-alkyl amide or its $(C_1-C_8)$-alkyl ester or its $(C_6-C_{14})$-aryl-$(C_1-C_4)$-alkyl ester. In this context, the radical of an α-amino acid representing —$NHR^{14}$ is obtained formally by abstracting a hydrogen atom from the amino group of the amino acid. Among these compounds, those which are very particularly preferred are compounds of the general formula I in which $R^3$ represents $CONHR^{14}$, where —$NHR^{14}$ represents the radical of the α-amino acids valine, lysine, phenylglycine, phenylalanine or tryptophan, or their $(C_1-C_8)$-alkyl esters or $(C_6-C_{14})$-aryl-$(C_1-C_4)$-alkyl esters.

Compounds which are preferred in addition to this are those of the general formula I in which, at the same time, W represents $R^1$—A—$C(R^{13})$;

Y represents a carbonyl group;

Z represents $N(R^0)$;

A represents a 1,4-phenylene radical;

B represents a methylene radical;

D represents $C(R^2)(R^3)$;

E represents $R^{10}CO$;

R and $R^0$, independently of each other, represent hydrogen or $(C_1-C_4)$-alkyl, in particular hydrogen, methyl or ethyl;

$R^1$ represents $H_2N-C(=NH)$, $H_2N-C(=NH)-NH$ or $H_2N-CH_2$;

$R^2$ represents hydrogen;

$R^3$ represents the radical $CONHR^{14}$;

$R^{10}$ represents hydroxyl or $(C_1-C_8)$-alkoxy, preferably $(C_1-C_4)$-alkoxy;

$R^{13}$ represents $(C_1-C_6)$-alkyl, $(C_3-C_7)$-cycloalkyl or benzyl, in particular methyl;

$R^{14}$ represents methyl which is substituted by phenyl and hydroxycarbonyl, or represents methyl which is substituted by phenyl and $(C_1-C_8)$-alkoxycarbonyl, preferably $(C_1-C_4)$-alkoxycarbonyl;

b, c and d represent 1 and e, f and g represent 0;

h represents 1 or 2, and preferably represents 1.

If $-NHR^{14}$ represents a $(C_1-C_8)$-alkyl ester of an α-amino acid, or if $R^{14}$ contains an alkoxycarbonyl radical, the methyl, ethyl, isopropyl, isobutyl or tert-butyl ester is then preferred; if $-NHR^{14}$ represents a $(C_6-C_{14})$-aryl-$(C_1-C_4)$-alkyl ester of an α-amino acid, the benzyl ester is then preferred.

Particularly preferred compounds of the general formula I are furthermore those in which W represents $R^1-A-CH=C$ and in this A represents a phenylene radical, or W represents $R^1-A-C(R^{13})$ and in this A represents a divalent radical from the group methylene, ethylene, trimethylene, tetramethylene, cyclohexylene, phenylene or phenylenemethyl;

B represents a divalent radical from the group methylene, ethylene, trimethylene, tetramethylene, vinylene or phenylene;

E denotes $R^{10}CO$;

R and $R^0$ denote, independently of each other, hydrogen or $(C_1-C_6)$-alkyl;

$R^1$ represents $X-NH-C(=NH)$, $X-NH-C(=NX)-NH$ or $X-NH-CH_2$;

X represents hydrogen, $(C_1-C_6)$-alkylcarbonyl, $(C_1-C_6)$-alkoxycarbonyl, $(C_1-C_8)$-alkylcarbonyloxy-$(C_1-C_6)$-alkoxycarbonyl or $(C_6-C_{14})$-aryl-$(C_1-C_6)$-alkoxycarbonyl;

$R^2$ represents hydrogen or $(C_1-C_8)$-alkyl;

$R^3$ represents $CONHR^{15}$;

$R^{15}$ represents $R^{16}$-$(C_1-C_6)$-alkyl or $R^6$, where $R^{16}$ represents a 7- to 12-membered bridged bicyclic or tricyclic radical which is saturated or partially unsaturated and which can also contain one to four identical or different heteroatoms from the group nitrogen, oxygen and sulphur and which can also be substituted by one or more identical or different substituents from the group $(C_1-C_4)$-alkyl and oxo, and, in particular, $R^{15}$ represents an adamantyl radical or an adamantylmethyl radical;

and e, g and h, independently of each other, represent integers from 0 to 3, and b, c and d represent 1.

Among these particularly preferred compounds of the general formula I, containing a bicyclic or tricyclic radical representing $R^{16}$, those are very particularly preferred in which, at the same time, W represents $R^1-A-C(R^{13})$;

Y represents a carbonyl group;

Z represents $N(R^0)$;

A represents a 1,4-phenylene radical;

B represents a methylene radical;

D represents $C(R^2)(R^3)$;

E represents $R^{10}CO$;

R and $R^0$, independently of each other, represent hydrogen or $(C_1-C_4)$-alkyl, in particular hydrogen, methyl or ethyl;

$R^1$ represents $H_2N-C(=NH)$, $H_2N-C(=NH)-NH$ or $H_2N-CH_2$;

$R^2$ represents hydrogen;

$R^3$ represents the radical $CONHR^{15}$;

$R^{10}$ represents hydroxyl or $(C_1-C_8)$-alkoxy, preferably $(C_1-C_4)$-alkoxy;

$R^{13}$ represents $(C_1-C_6)$-alkyl, $(C_3-C_7)$-cycloalkyl or benzyl, in particular methyl;

$R^{15}$ represents an adamantyl radical or an adamantylmethyl radical;

b, c and d represent 1 and e, f and g represent 0;

h represents 1 or 2, and preferably represents 1.

Furthermore, particularly preferred compounds of the general formula I are also those in which, at the same time, W represents $R^1-A-C(R^{13})$;

Y represents a carbonyl group;

Z represents $N(R^0)$;

A represents a 1,4-phenylene radical;

B represents a methylene radical;

D represents $C(R^2)(R^3)$;

E represents $R^{10}CO$;

R and $R^0$, independently of each other, represent hydrogen or $(C_1-C_4)$-alkyl, in particular hydrogen, methyl or ethyl;

$R^1$ represents $H_2N-C(=NH)$, $H_2N-C(=NH)-NH$ or $H_2N-CH_2$;

$R^2$ represents hydrogen;

$R^3$ represents an unsubstituted phenyl radical or naphthyl radical, a phenyl radical or naphthyl radical which is substituted by one, two or three identical or different radicals from the group $(C_1-C_4)$-alkyl, $(C_1-C_4)$-alkoxy, hydroxyl, halogen, trifluoromethyl, nitro, methylenedioxy, hydroxycarbonyl, $(C_1-C_4)$-alkoxycarbonyl, aminocarbonyl, cyano, phenyl, phenoxy and benzyloxy, a pyridyl radical, a $(C_1-C_4)$-alkyl radical, a $(C_2-C_4)$-alkenyl radical, a $(C_2-C_4)$-alkynyl radical or a $(C_5-C_6)$-cycloalkyl radical, and, in particular $R^3$ represents a phenyl radical;

$R^{10}$ represents hydroxyl or $(C_1-C_8)$-alkoxy, in particular $(C_1-C_4)$-alkoxy, and, preferably $R^{10}$ represents a radical from the group hydroxyl, methoxy, ethoxy, propoxy and isopropoxy;

$R^{13}$ represents $(C_1-C_6)$-alkyl, $(C_3-C_7)$-cycloalkyl or benzyl, in particular methyl;

b, c and d represent 1, and e, f and g represent 0;

h represents 1 or 2; and preferably represents 1.

Among these particularly preferred compounds of the general formula I those are very particularly preferred in which, at the same time, W represents $R^1$—A—$C(CH_3)$;

Y represents a carbonyl group;

Z represents NH;

A represents a 1,4-phenylene radical;

$R^1$ represents an amino-imino-methyl radical;

B represents a methylene radical;

D represents CH(phenyl);

E represents hydroxycarbonyl, methoxycarbonyl, ethoxycarbonyl or isopropoxycarbonyl;

R represents hydrogen;

b, c, d and h represent 1, and e, f and g represent 0.

Of these very particularly preferred compounds, those are preferred over and above this which in each case have a uniform configuration at the chiral centre in the 4 position of the imidazolidine ring and the chiral carbon atom representing D, and in particular have the S configuration at the carbon atom representing D.

Also, in all the preferred embodiments, the present invention naturally embraces, as has already been mentioned above, the physiologically tolerated salts of the compounds.

Compounds of the formula I can be prepared, for example, by fragment condensation of a compound of the general formula II

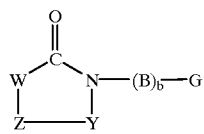
(II)

with a compound of the general formula III,

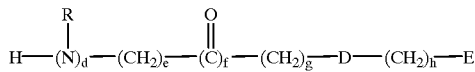
(III)

in which W, Y, Z, B, D, E and R, and also b, d, e, f, g and h, are defined as indicated above, and G represents hydroxycarbonyl, ($C_1$–$C_6$)-alkoxycarbonyl, activated carboxylic acid derivatives, such as acid chlorides, active esters or mixed anhydrides, or represents isocyanato.

In order to condense the compounds of the general formula II with those of the general formula III, use is advantageously made of the coupling methods of peptide chemistry which are known per se (see, for example, Houben-Weyl, Methoden der Organischen Chemie, (Methods of organic chemistry), Volumes 15/1 and 15/2, Stuttgart, 1974). For this purpose, it is necessary, as a rule, for non-reacting amino groups which are present to be protected during the condensation by reversible protective groups. This is also the case for the carboxyl groups of the compounds of the formula III, which are preferably present as ($C_1$–$C_6$)-alkyl esters, benzyl esters or tert-butyl esters. An amino-group protection is not necessary when the amino groups to be generated are still present as nitro groups or cyano groups and are only formed by hydrogenation after the coupling. After the coupling, the protective groups which are present are eliminated in a suitable manner. For example, $NO_2$ groups (guanidino protection), benzyloxycarbonyl groups and benzyl esters can be removed by hydrogenation. The protective groups of the tert-butyl type are cleaved acidically, while the 9-fluorenylmethyloxycarbonyl radical is removed by secondary amines.

The compounds of the general formula I, in which the 5-membered ring heterocycle represents a dioxo- or thioxo-oxo-substituted imidazolidine ring, in which W represents $R^1$—A—$C(R^{13})$, may also be obtained as follows:

By reacting α-amino acids or N-substituted α-amino acids, or, preferably, their esters, e.g. the methyl, ethyl, tert-butyl or benzyl ester, for example a compound of the general formula IV,

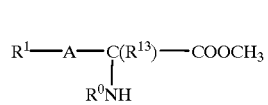
(IV)

in which $R^0$, $R^1$, $R^{13}$ and A are defined as indicated above, with an isocyanate or isothiocyanate, for example of the general formula V,

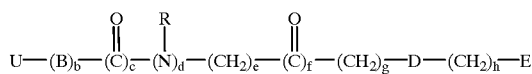
(V)

in which B, D, E and R, and also b, c, d, e, f, g and h, are defined as indicated above, and U denotes isocyanato, isothiocyanato or trichloromethylcarbonylamino, urea derivatives or thiourea derivatives, for example of the general formula VI,

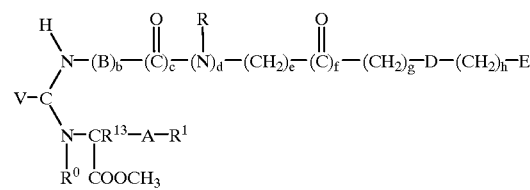
(VI)

for which the abovementioned definitions apply, and in which V denotes oxygen or sulphur, are obtained, which derivatives are cyclized by heating with acid, with hydrolysis of the ester functions, to yield compounds of the general formula Ia

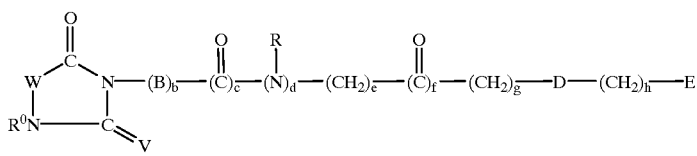

(Ia)

in which V denotes oxygen or sulphur and W represents $R^1$—A—$C(R^{13})$, and for which the abovementioned definitions otherwise apply.

During the cyclization, guanidino groups can be blocked by protective groups, such as $NO_2$ or Mtr. Amino groups in the side chain can likewise be present in protected form (for example as Boc or Z derivatives) or still be present as a $NO_2$ or cyano function which can subsequently be reduced to the amino group or, in the case of the cyano group, also be converted into the amidino group.

Another method of preparing compounds of the general formula Ia, in which V denotes oxygen or sulphur and W represents $R^1$—A—$C(R^{13})$, and for which the abovementioned definitions otherwise apply, is the reaction of compounds of the general formula VII,

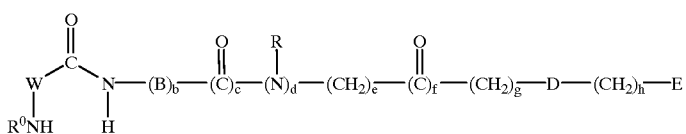

(VII)

in which W represents $R^1$—A—$C(R^{13})$, and for which the abovementioned definitions otherwise apply, with phosgene, thiophosgene or corresponding equivalents (in analogy with S. Goldschmidt and M. Wick, Liebigs Ann. Chem. 575 (1952), 217–231, and C. Tropp, Chem. Ber. 61 (1928), 1431–1439).

The following reagents can be used for the guanylation and nitroguanylation of the amino function:

1. O-Methylisourea (S. Weiss and H. Krommer, Chemiker-Zeitung 98 (1974) 617–618),
2. S-Methylisothiourea R. F. Borne, M. L. Forrester and I. W. Waters, J. Med. Chem. 20 (1977) 771–776),
3. Nitro-S-methylisothiourea (L. S. Hafner and R. E. Evans, J. Org. Chem. 24 (1959) 1157),
4. Formamidinesulphonic acid (K. Kim, Y.-T. Lin and H. S. Mosher, Tetrahedron Lett. 29 (1988) 3183–3186),
5. 3,5-Dimethyl-1-pyrazolylformamidinium nitrate (F. L. Scott, D. G. O'Donovan and J. Reilly, J. Amer. Chem. Soc. 75 (1953) 4053–4054),
6. N,N'-Di-tert-butyloxycarbonyl-S-methylisothiourea (R. J. Bergeron and J. S. McManis, J. Org. Chem. 52 (1987) 1700–1703),
7. N-Alkoxycarbonyl-, N,N'-dialkoxycarbonyl-, N-alkylcarbonyl- and N,N'-dialkylcarbonyl-S-methylisothiourea (H. Wollweber, H. Kölling, E. Niemers, A. Widding, P. Andrews, H.-P. Schulz and H. Thomas, Arzneim. Forsch./Drug Res. 34 (1984) 531–542).

Amidines can be prepared from the corresponding cyano compounds by adding on alcohols (e.g. methanol or ethanol) in acidic, anhydrous medium (e.g. dioxane, methanol or ethanol) and subsequent aminolysis, e.g. by treating with ammonia in alcohols such as, for example, isopropanol, ethanol or methanol (G. Wagner, P. Richter and Ch. Garbe, Pharmazie 29 (1974) 12–15). Another method of preparing amidines is to add $H_2S$ onto the cyano group, followed by a methylation of the resulting thioamide and subsequent reaction with ammonia (GDR patent No. 235 866).

The compounds of the general formula I, and their physiologically tolerated salts, can be administered to animals, preferably mammals, and, in particular, humans, as medicines on their own, in mixtures with each other, or in the form of pharmaceutical preparations which permit enteral or parenteral use and which contain, as the active constituent, an effective dose of at least one compound of the general formula I, or a salt thereof, in addition to customary pharmaceutically acceptable excipients and additives. The preparations normally contain from about 0.5 to 90% by weight of the therapeutically active compound.

The medicines can be administered orally, for example in the form of pills, tablets, lacquered tablets, coated tablets, granules, hard and soft gelatine capsules, solutions, syrups, emulsions or suspensions, or aerosol mixtures. However, the administration can also be effected rectally, e.g. in the form of suppositories, or parenterally, e.g. in the form of injection solutions or infusion solutions, microcapsules or rods, or percutaneously, e.g. in the form of ointments or tinctures, or nasally, e.g. in the form of nasal sprays.

The pharmaceutical preparations are produced in a manner known per se, with pharmaceutically inert inorganic or organic excipients being used. For example, lactose, corn starch, or derivatives thereof, talc, stearic acid or its salts, etc., can be used for producing pills, tablets, coated tablets and hard gelatine capsules. Examples of excipients for soft gelatine capsules and suppositories are fats, waxes, semi-solid and liquid polyols, natural or hardened oils, etc. Suitable excipients for preparing solutions and syrups are, for example, water, sucrose, invert sugar, glucose, polyols, etc. Suitable excipients for producing injection solutions are water, alcohols, glycerol, polyols, vegetable oils, etc. Suitable excipients for microcapsules, implants or rods are mixed polymers of glycolic acid and lactic acid.

In addition to the active compounds and excipients, the pharmaceutical preparations can also contain additives, such as, for example, fillers, extenders, disintegrants, binding agents, glidants, wetting agents, stabilizers, emulsifiers, preservatives, thickeners, diluents or buffering substances, and, additionally, solvents or solubilizers or agents for achieving a depot effect, and also salts for altering the osmotic pressure, coating agents or antioxidants. They can also contain two or more compounds of the general formula I or their pharmacologically acceptable salts and one or more different therapeutically active compounds in addition.

Examples of different therapeutically active substances of this nature are blood flow-promoting agents, such as dihydroergocristine, nicergoline, buphenine, nicotinic acid and its esters, pyridylcarbinol, bencyclane, cinnarizine, naftidrofuryl, raubasine and vincamine; positively inotropic compounds, such as digoxin, acetyldigoxin, metildigoxin and lanato-glycosides; coronary dilating agents, such as carbocromen; dipyridamole, nifedipine and perhexiline; anti-anginous compounds, such as isosorbide dinitrate, isosorbide mononitrate, glycerol nitrate, molsidomine and verapamil; β-blockers, such as propranolol, oxprenolol, atenolol, metroprolol and penbutolol. In addition to this, the compounds can also, for example, be combined with nootropically active substances, such as, for example, piracetam, or substances with CNS activity, such as pirlindole, sulpiride, etc.

The dose can be varied within wide limits and must be adjusted to the individual circumstances in each specific case. In general, a daily dose of from about 0.1 to 1 mg/kg, preferably of from 0.3 to 0.5 mg/kg, of bodyweight is appropriate for achieving effective results in the case of oral administration, and, in the case of intravenous administration the daily dose is, in general, from about 0.01 to 0.3 mg/kg, preferably from 0.05 to 0.1 mg/kg, of bodyweight. Particularly when relatively large quantities are being administered, the daily dose can be subdivided into several, e.g. 2, 3 or 4, smaller doses which are administered separately. Where appropriate, it can be necessary, depending on the individual response, to deviate upwards or downwards from the daily dose indicated. Normally, pharmaceutical preparations contain from 0.2 to 50 mg, preferably from 0.5 to 10 mg, of active compound of the general formula I, or of one of its pharmaceutically acceptable salts, per dose.

The compounds of the general formula I according to the invention have the ability to inhibit the cell/cell adhesion which is based on the interaction of Arg-Gly-Asp-containing proteins, such as fibronectin, fibrinogen or the von Willebrand factor, with the so-called integrins. Integrins are transmembrane glycoproteins, receptors for Arg-Gly-Asp-containing proteins (E. Ruoslahti and M. D. Pierschbacher, Science 238 (1987) 491–497; D. R. Phillips, I. F. Charo, L. V. Parise and L. A. Fitzgerald, Blood 71 (1988) 831–843). In addition, they inhibit the binding of other adhesive proteins such as vitronectin, collagen and laminin to the corresponding receptors on the surface of different cell types.

The compounds of the general formula I according to the invention inhibit thrombocyte aggregation, the metastasization of carcinoma cells and also the binding of osteoclasts to bone surfaces.

The compounds of the general formula I are used acutely when there is danger of thrombosis and chronically in the prevention of arteriosclerosis and thrombosis, e.g. in the therapy and prophylaxis of arterial blood vessel diseases, as in acute myocardial infarction, secondary prevention of myocardial infarction, reocclusion prophylaxis following lysis and dilatation (PTCA), unstable angina pectoris, transitory ischaemic attacks, stroke, coronary bypass operations including reocclusion prophylaxis in association with bypass, pulmonary embolism, peripheral occlusive arterial disease and dissecting aneurism; in the therapy of venous and microcirculatory blood vessel diseases, such as deep vein thrombosis, disseminated intravascular coagulation, post-operative and post-partum trauma, surgical or infectious shock, or septicaemia, or in diseases with hyperreactive thrombocytes, thrombotic thrombocytopenic purpura, preeclampsia, premenstrual syndrome, dialysis or extracorporeal circulation; a further application is in the treatment of cancer, e.g. during cancer operations and also prophylactically in association with cancer. Furthermore, osteoporosis can be prevented by inhibiting the binding of osteoclasts to the bone surface.

The compounds are tested, in particular, for their inhibitory effect in blood platelet aggregation and the attachment of fibrinogen to blood platelets (use is made of gel-filtered blood platelets from human donor blood which are activated with ADP or thrombin), and also for their in-vivo effect in inhibiting thrombocyte aggregation and thrombosis.

Test Method 1

As a functional test, measurement is made of the inhibition of the aggregation of gel-filtered human thrombocytes, following stimulation with ADP or thrombin, by the compounds according to the invention. The value given is the $IC_{50}$ value of the inhibition [Literature: Marguerie, G. A. et al., J. Biol. Chem. 254, 5357–5363 (1979); Marguerie, G. A. et al., J. Biol. Chem. 255, 154–161 (1980)].

For this purpose, human thrombocytes were isolated from platelet-rich plasma (PRP) by gel filtration on Sepharose 2 B. The resulting suspension of gel-filtered platelets (GFP), which contained $3 \times 10^8$ platelets/ml, was activated in the presence of 1 mg/ml of fibrinogen either with 10 μM ADP or with 0.1 U/ml thrombin, and stirred in an aggregometer (PAP 4, Biodata, Hatboro, Pa., USA) at 37° C. and at 1000 revolutions per minute. The maximum increase in the translucency is taken as a measure of the aggregation. The test substances were added to the GFP at 37° C. and 2 min before activating with ADP or thrombin. The inhibition of the aggregation is given as an $IC_{50}$ value, i.e. as the average concentration of test substance which is required in order to elicit a 50% inhibition in GFP samples from 2–4 different donors (semilogarithmic dose/effect relationship).

In this test, the following results were obtained for the compounds of the examples below:

| Example | ADP-stimulated $IC_{50}$ (μM) | Thrombin-stimulated $IC_{50}$ (μM) |
|---|---|---|
| 1 | 0.04 | 0.05 |
| 6 | 2.5 | 0.8 |
| 7 | 0.3 | 0.3 |
| 6 | 0.15 | 0.1 |
| 9 | 1.0 | 0.5 |
| 10 | 0.15 | 0.06 |
| 13 | 0.2 | 0.2 |
| 20 | 2.0 | 1.0 |
| 21 | 0.8 | 0.5 |
| 22 | 0.025 | 0.05 |
| 23 | 0.03 | 0.05 |
| 24 | 0.055 | 0.08 |
| 25 | 0.03 | 0.05 |
| 26 | 0.02 | 0.04 |
| 27 | 0.025 | 0.04 |
| 28 | 0.025 | 0.04 |
| 29 | 0.05 | 0.04 |
| 30 | 0.5 | 0.4 |
| 31 | 3 | 0.6 |
| 32 | 0.2 | 0.15 |
| 33 | 0.5 | 0.2 |
| 34 | 2.5 | 1.5 |
| 35 | 0.1 | 0.3 |
| 36 | 0.2 | 0.15 |
| 37 | 0.1 | 0.2 |
| 38 | 0.3 | 0.35 |
| 39 | 0.08 | 0.15 |

-continued

| Example | ADP-stimulated IC$_{50}$ ($\mu$M) | Thrombin-stimulated IC$_{50}$ ($\mu$M) |
|---|---|---|
| 40 | 0.4 | 0.25 |
| 41 | 0.1 | 0.15 |
| 42 | 0.3 | 0.2 |
| 43 | 0.5 | 0.5 |
| 44 | 0.4 | 0.2 |
| 45 | 0.2 | 0.2 |
| 46 | 0.1 | 0.1 |
| 47 | 0.1 | 0.15 |
| 48 | 2.0 | 0.8 |
| 49 | 0.6 | 0.2 |
| 50 | 0.55 | 0.4 |
| 52 | 0.5 | 0.4 |
| 56 | 0.1 | 0.06 |
| 57 | 6 | 5 |
| 58 | 0.02 | 0.025 |
| 59 | 50 | 40 |
| 60 | 5 | 4 |
| 67 | 0.08 | 0.2 |
| 68 | 0.05 | 0.045 |
| 69 | 0.025 | 0.045 |
| 70 | 0.065 | 0.07 |

Test Method 2

The inhibition of the binding of fibrinogen to its receptor (glycoprotein IIb/IIIa) by the compounds according to the invention is tested on intact, gel-filtered human thrombocytes. The value given is the K$_i$ value for inhibition of the binding of $^{125}$I-fibrinogen following stimulation with ADP (10 $\mu$M) [Literature: Bennett, J. S.; Vilaire, G. J. Clin. Invest. 64, 1393–1401 (1979); Kornecki, E. et al., J. Biol. Chem. 256, 5696–5701 (1981)].

For this purpose, human thrombocytes were isolated from platelet-rich plasma (PRP) by gel filtration on Sepharose 2 B. A suspension of gel-filtered platelets (GFP) was obtained which contained 4×10 platelets/ml. The platelets were incubated at room temperature for 30 min in the presence of 40 nmol/l $^{125}$I-fibrinogen, 10 $\mu$M ADP and different concentrations of the test substance. Aliquots of 100 $\mu$l were then added onto 20% sucrose, and the platelets were sedimented by being centrifuged for 2 minutes at 12,000 revolutions per minute. The supernatant was decanted carefully and completely and the remaining sediment was measured in a gamma counter. The specific binding was ascertained by subtracting the binding in the presence of an excess (10 $\mu$M) of unlabelled fibrinogen from the total bound radioactivity. The binding is given in fmol of $^{125}$I-fibrinogen/$10^8$ platelets. The dissociation constant K$_i$ for the test substance was determined from the $^{125}$I-fibrinogen vs. (non-labelled) test substance displacement experiments by a computer analysis of the binding data (sigma plot).

In this test, the following results were obtained for the compounds of the examples below:

| Example: | K$_i$ ($\mu$M), ADP-stimulated |
|---|---|
| 1 | 0.0132 |
| 56 | 0.0218 |
| 57 | 1.97 |
| 58 | 0.0092 |

Test Method 3

The inhibition of the binding of fibrinogen to its receptor (glycoprotein IIb/IIIa) which is brought about by the compounds according to the invention is tested on the isolated receptor, which was isolated from human thrombocytes and immobilized in microtitre plates. The value given is the K$_i$ value of the inhibition of the binding of $^{125}$I-fibrinogen [Literature: Fitzgerald, L. A. et al., Anal. Biochem. 151, 169–177 (1985) Pytela, R. et al., Science 231, 1559–1562 (1986); Charo, I. F. et al., J. Biol. Chem. 266, 1415–1421 (1991); Scarborough, R. M. et al., J. Biol. Chem. 266, 9359–9362 (1991)]. In this test, the following results were obtained for the compounds of the examples below:

| Example: | K$_i$ (nM), ADP-stimulated |
|---|---|
| 1 | 0.172 |
| 13 | 0.748 |
| 21 | 1.9 |
| 22 | 0.15 |
| 25 | 0.175 |
| 27 | 0.107 |
| 26 | 0.117 |
| 28 | 0.078 |
| 39 | 0.948 |
| 40 | 1.99 |
| 46 | 1.23 |
| 56 | 0.466 |
| 57 | 37.3 |
| 58 | 0.172 |

EXAMPLES

The products were identified by way of mass spectra and/or NMR spectra.

Example 1

((R,S)-4-(4-(Aminoiminomethyl)phenyl)-4-methyl-2,5-dioxoimidazolidin-1-yl)-acetyl-L-aspartyl-L-phenylglycine 1a. (R,S)-4-(4-Cyanophenyl)-4-methyl-2,5-dioxoimidazolidine 20 g (138 mmol) of p-acetylbenzonitrile, 115.6 g of ammonium carbonate (1.21 mol) and 11.6 g of potassium cyanide (178 mmol) are dissolved in 600 ml of a mixture consisting of 50% ethanol and 50% water. The mixture is stirred at 55° C. for 5 hours and left to stand at room temperature overnight. The solution is adjusted to pH=6.3 with 6 N HCl and subsequently stirred at room temperature for 2 hours. The precipitate is filtered off with suction, washed with water and dried over phosphorus pentoxide under high vacuum.

Yield: 22.23 g (75%).

1b. Methyl ((R,S)-4-(4-cyanophenyl)-4-methyl-2,5-dioxoimidazolidin-1-yl)acetate 1.068 g of sodium (46.47 mmol) are dissolved, under nitrogen, in 110 ml of abs. methanol. 10 g of (R,S)-4-(4-cyano-phenyl)-4-methyl-2,5-dioxoimidazolidine (46.47 mmol) are added to the clear solution and the mixture is boiled under reflux for 2h. 7.75 g (46.48 mmol) of potassium iodide are added and a solution of 4.53 ml of methyl chloroacetate (51.3 mmol) in 5 ml of methanol is added dropwise within the space of one hour. The mixture is heated to boiling for 6 hours, left to stand at room temperature overnight, and then concentrated. The oily residue is chromatographed on silica gel using methylene chloride/ethyl acetate (9:1).

Yield: 8.81 g (66%).

1c. Methyl ((R,S)-4-(4-(ethoxyiminomethyl)phenyl)-4-methyl-2.5-dioxoimidazolidin-1-yl)acetate hydrochloride A suspension of 4 g of methyl ((R,S)-4-(4-cyanophenyl)-4-methyl-2,5-dioxoimidazolidin-1-yl)acetate (13.92 mmol) is 60 ml of abs. ethanol is cooled down to 0° C. Dry HCl gas is passed into the suspension, with the temperature being kept under 10° C. all the time, until the nitrile band is no longer present in the IR spectrum. 200 ml of diethyl ether are added to the ethanolic solution and the mixture is left to stand at 4° C. overnight. The precipitate is filtered off with suction and dried under high vacuum.

Yield: 3.96 g (77%).

1d. Methyl ((R,S)-4-(4-(aminoiminomethyl)-phenyl)-4-methyl-2.5-dioxoimidazolidin-1-yl)acetate hydrochloride 3.96 g of methyl ((R,S)-4-(4-(ethoxyiminomethyl) phenyl)-4-methyl-2,5-dioxoimidazolidin-1-yl)acetate hydrochloride (10.7 mmol) are suspended in 40 ml of isopropanol and treated with 11.9 ml of a 2 N solution of ammonia in isopropanol. The reaction mixture is stirred at 50° C. for 2 hours. The mixture is cooled down and 200 ml of diethyl ether are then added to it. The precipitate is filtered off with suction and dried under high vacuum.

Yield: 3.27 g (89%).

1e. ((R,S)-4-(4-(Aminoiminomethyl)phenyl)-4-methyl-2,5-dioxoimidazolidin-1-y)acetic acid hydrochloride 3.27 g of methyl ((R,S)-4-(4-aminoiminomethyl) phenyl)-4-methyl-2,5-dioxoimidazolidin-1-yl)acetate hydrochloride (9.6 mmol) are dissolved in 50 ml of concentrated hydrochloric acid. The solution is heated to boiling for 6 hours and then concentrated.

Yield: 2.73 g (87%).

1f. ((R,S)-4-(4-(Aminoiminomethyl) phenyl)-4-methyl-2,5-dioxoimidazolidin-1-yl)acetyl-L-aspartyl-L-phenylglycine di-tert-butyl ester hydrochloride 673 mg of DCC (3.06 mmol) are added, at 0° C., to a solution of 1 g of ((R,S)-4-(4-(aminoiminomethyl) phenyl-4-methyl-2,5-dioxoimidazolidin-1-yl)acetic acid hydrochloride (3.06 mmol), 1.27 g of H-Asp(OBu$^t$)-Phg-OBu$^t$ hydrochloride (3.06 mmol) and 413 mg of HOBt in 10 ml of dimethylformamide. The mixture is left to stir at 0° C. for one hour and at room temperature for 4 hours. Subsequently, the mixture is left to stand in a cold room over the weekend and the precipitate is then filtered off with suction and the filtrate concentrated. For purification, the substance is chromatographed on silica gel using methylene chloride/methanol/glacial acetic acid/water (8.5:1.5:0.15:0.15).

Yield: 920 mg of oil (still contains acetic acid).

1g. ((R,S)-4-(4-Aminoiminomethyl)phenyl)-4-methyl-2,5-dioxoimidazolidin-1-yl)acetyl-L-aspartyl-L-phenylglycine 920 mg of ((R,S)-4-(4-(aminoiminomethyl)phenyl)-4-methyl-2,5-dioxoimidazolidin-1-yl)acetyl-L-aspartyl-L-phenylglycine ditert-butyl ester hydrochloride are dissolved in a mixture consisting of 5.4 ml of trifluoroacetic acid, 0.6 ml of water and 0.6 ml of dimercaptoethane. The solution is left to stand at room temperature for one hour and is then concentrated under a water suction vacuum. For purification, the substance is chromatographed on Sephadex LH20 using a mixture of glacial acetic acid, n-butanol and water. The fractions containing the pure substance are concentrated. The residue is dissolved in water and freeze-dried.

Yield; 390 mg $[\alpha]_D$=+1.3° (c=1, in methanol, 25° C.).

Example 2

((R,S)-4-(4-(Aminoiminomethyl)phenyl)-3,4-dimethyl-2,5-dioxoimidazolidin-1-yl)acetyl-L-aspartyl-L-phenylglycine 2a. Methyl ((R,S)-4-(4-cyanophenyl)-3,4-dimethyl-2,5-dioxoimidazolidin-1-yl)acetate 3 g of methyl ((R,S)-4-(4-cyanophenyl)-4-methyl-2,5-dioxoimidazolidin-1-yl)acetate (10.4 mmol) are dissolved, under argon, in 15 ml of anhydrous dimethylformamide. 275.5 mg of a dispersion of sodium hydride in mineral oil (11.4 mmol) are added in an argon countercurrent. The reaction mixture is stirred at room temperature for 15 minutes. Subsequently, 721 μm of methyl iodide (11.4 mmol) are added. The mixture is stirred at room is temperature for 4 hours and is then left to stand at room temperature overnight. The solution is concentrated. For purification, the substance is chromatographed on silica gel using methylene chloride/ethyl acetate (9.5:0.5). The fractions containing the pure substance are concentrated.

Yield: 2.14 g of oil (68%).

2b. Methyl ((R,S)-4-(4-(ethoxyiminomethyl)phenyl)-3,4-dimethyl-2,5-dioxoimidazolidin-1-yl) acetate hydrochloride A solution of 2.56 g of methyl ((R,S)-4-(4-cyanophenyl)-3,4-dimethyl-2,5-dioxoimidazolidin-1-yl)acetate (8.5 mmol) in 40 ml of abs. ethanol is cooled down to 0° C. Dry HCl gas is passed into the solution, with the temperature being kept below 10° C. all the time, until the nitrile band is no longer present in the IR spectrum. The ethanolic solution is concentrated to 20 ml and then treated with 200 ml of diethyl ether. The suspension is concentrated and dried under high vacuum.

Yield: 2.27 g (76%).

2c. Methyl ((R,S)-4-(4-(aminoiminomethyl)phenyl)-3,4-dimethyl-2,5-dioxoimidazolidin-1-yl)acetate hydrochloride 2.26 g of methyl ((R,S)-4-(4-(ethoxyiminomethyl) phenyl)-3,4-dimethyl-2,5-dioxoimidazolidin-1-yl)acetate hydrochloride (6.4 mmol) are suspended in 25 ml of isopropanol and treated with 7.2 ml of a 2 N solution of ammonia in isopropanol. The reaction mixture is stirred at 50° C. for 2.5 hours. The mixture is cooled down and 200 ml of diethyl ether are then added to it. The precipitate is filtered off with suction and dried under high vacuum.

Yield: 1.03 g (45%).

2d. ((R,S)-4-(4-(Aminoiminomethyl)phenyl)-3,4-dimethyl-2,5-dioxoimidazolidin-1-yl)acetic acid hydrochloride 1 g of methyl ((R,S)-4-(4-(aminoiminomethyl) phenyl)-3,4-dimethyl-2,5-dioxoimidazolidin-1-yl)acetate hydrochloride (3.14 mmol) is dissolved in 20 ml of concentrated hydrochloric acid. The solution is heated to boiling for 6 hours and then concentrated.

Yield: 770 mg (81%).

2e. ((R,S)-4-(4-(Aminoiminomethyl)phenyl)-3,4-dimethyl-2,5-dioxoimidazolidin-1-yl)acetyl-L-aspartyl-L-phenylglycine di-tert-butyl ester hydrochloride 220 mg of DCC (1 mmol) are added, at 0° C., to a solution of 340 mg of ((R,S)-4-(4-(aminoiminomethyl)phenyl)-3,4-dimethyl-2,5-dioxoimidazolidin-1-yl)acetic acid hydrochloride (1 mmol), 415 mg of H-Asp(OBu$^t$)-Phg-OBu$^t$ hydrochloride (1 mmol) and 135 mg of HOBt in 7 ml of dimethylformamide. 0.13 ml of N-ethyl-morpholine is added until a pH of 5.0 is achieved and the mixture is left stirring at 0° C. for one hour and at room temperature for 2 hours. Subsequently, the mixture is left to stand in a cold room over the weekend and the precipitate is then filtered off with suction and the filtrate concentrated. For purification, the substance is chromatographed on Sephadex LH20 using a mixture consisting of glacial acetic acid, n-butanol and water. The fractions containing the pure substance are concentrated. The residue is dissolved in water and freeze-dried.

Yield: 377 mg (57%).

2f. ((R,S)-4-(4-(Aminoiminomethyl)phenyl)-3,4-dimethyl-2,5-dioxoimidazolidin-1-yl)acetyl-L-aspartyl-L-phenylglycine 370 mg of ((R,S)-4-(4-(aminoiminomethyl) phenyl)-3,4-dimethyl-2,5-dioxoimidazolidin-1-yl)acetyl-L-aspartyl-L-phenyl-glycine di-tert-butyl ester hydrochloride (0.53 mmol) are dissolved in a mixture consisting of 3.6 ml of trifluoroacetic acid, 0.4 ml of water and 0.4 ml of dimercaptoethane. The solution is left to stand at room temperature for one hour and is then concentrated under a water suction vacuum. For purification, the substance is chromatographed on Sephadex LH20 using a mixture of glacial acetic acid, n-butanol and water. The fractions containing the pure substance are concentrated. The residue is dissolved in water and freeze-dried.

Yield: 210 mg of a white solid (72%).

$[a]_D = -2.8°$ (c=1, in methanol, 23° C.).

Example 3

((R,S)-4-(4-(Aminoiminomethyl)phenyl)-4-methyl-2,5-dioxoimidazolidin-1-yl)acetyl-L-aspartyl-L-phenylglycine dimethyl ester hydrochloride 977 mg of DCC (5.66 mmol) are added, at 0° C., to a solution of 1.47 g of ((R,S)-4-(4-(aminoiminomethyl)phenyl)-4-methyl-2,5-dioxoimidazolidin-1-yl)acetic acid hydrochloride (4.4 mmol), 1.45 g of H-Asp(OMe)-Phg-OMe hydrochloride (4.4 mmol) and 600 mg of HOBt in 15 ml of dimethylformamide. The mixture is left stirring at 0° C. for one hour and at room temperature for 8 hours. The precipitate is filtered off with suction and the filtrate is concentrated. For purification, the substance is chromatographed on silica gel using methylene chloride/methanol/-glacial acetic acid/water (8:2:0.15:0.15), and subsequently in methylene chloride/methanol/glacial acetic acid (30:10:0.5). The fractions containing the pure substance are concentrated. The residue is dissolved in water and freeze-dried.

Yield: 437 mg of a white solid (16%).

Example 4

((R,S)-4-(4-(Aminoiminomethyl)phenyl)-4-methyl-2,5-dioxoimidazolidin-1-yl)acetyl-L-aspartyl-L-phenylglycine diisopropyl ester hydrochloride 4a. (N-Benzyloxycarbonyl)-L-phenylglycine isopropyl ester 20 g of Z-Phg-OH (70 mmol) are dissolved in a mixture consisting of 26 ml of isopropanol and 26 ml of pyridine. A solution of 31.5 ml of 50% propanephosphonic anhydride in ethyl acetate and 350 mg of DMAP are added and the mixture is stirred at room temperature for 24 hours. The mixture is subsequently concentrated in vacuo and the residue is partitioned between ethyl acetate and water. The organic phase is extracted by shaking with a solution of potassium hydrogen sulphate (100 g of potassium sulphate and 50 g of potassium hydrogen sulphate dissolved in 1 liter of water), with a solution of sodium hydrogen carbonate and with water. The organic phase is dried over sodium sulphate and concentrated.

Yield: 16.74 g of oil (73%).

4b. L-Phenylglycine isopropyl ester hydrochloride 16.74 g of (N-benzyloxycarbonyl)-L-phenylglycine isopropyl ester (51 mmol) are dissolved in methanol and hydrogenated catalytically over Pd/active charcoal at a pH of 4.6 using an automated burette and while adding 2 N methanolic HCl. The catalyst is filtered off with suction through kieselguhr and the filtrate is concentrated. The residue is triturated with diethyl ether.

Yield: 9.21 g of a white solid (79%).

4c. $C_\beta$-Isopropyl L-aspartate hydrochloride 31 ml (0.16 mol) of thionyl chloride are added slowly to 1000 ml of isopropanol which have been cooled down to −10° C. 40 g of L-aspartic acid (0.3 mol) are then introduced into the solution. The mixture is stirred at 40° C. for 6 hours. Subsequently, the mixture is left to stand at room temperature over the weekend. The solution is concentrated down to a volume of 250 ml and 500 ml of diethyl ether are then added to it. The precipitate is filtered off with suction. The filtrate is concentrated further and additional crude product is precipitated out by adding diethyl ether. For purification, 20 g of the crude product are purified on a column containing 1 kg of acidic aluminium oxide.

Yield: 8.55 g

4d. $C_\beta$-Isopropyl (N-benzyloxycarbonyl)-L-aspartate cyclohexylamine salt 8.55 g of $C_\beta$-isopropyl L-aspartate hydrochloride (48.8 mmol) are dissolved in a mixture consisting of 110 ml of water and 110 ml of dioxane, and 4.1 g (48.8 mmol) of sodium hydrogen carbonate are then added. 13.4 g of N-(benzyloxy-carbonyloxy) succinimide (53.8 mmol) are added, and the mixture is stirred at room temperature for 1 hour. The pH is adjusted to a value of 8 by adding 10 g of sodium hydrogen carbonate. The mixture is stirred at room temperature for 5 hours and then concentrated. The residue is partitioned between ethyl acetate and 2 N HCl. The organic phase is extracted by shaking with water, dried over sodium sulphate, and concentrated. The resulting oil (12.35 g) is dissolved in 300 ml of diethyl ether. Cyclohexylamine is added dropwise to the solution until a pH of 8.0 is reached. The precipitate is filtered off with suction and washed with diethyl ether.

Yield: 12.84 g (64%).

4e. $C_\beta$-Isopropyl (N-benzyloxycarbonyl)-L-aspartate 12.84 g of $C_\beta$-isopropyl (N-benzyloxycarbonyl)-L-aspartate cyclohexylamine salt (31.4 mmol) are suspended in 250 ml of ethyl acetate. The suspension is extracted by shaking with 15.7 ml of a 2 N sulphuric acid (31.4 mmol) and water until a clear solution is produced. The organic phase is washed with potassium hydrogen sulphate solution (100 g of potassium sulphate and 50 g of potassium hydrogen sulphate dissolved in 1 liter of water), dried over sodium sulphate, and concentrated.

Yield: 8.22 g of oil (85%).

4f. $C_\beta$-Isopropyl (N-benzyloxycarbonyl)-L-aspartate-L-phenylglycine isopropyl ester 3.36 ml of N-ethylmorpholine and 5.69 g of DCC (25.86 mmol) are added, at 0° C., to a solution of 8 g of Z-L-Asp(OiPr)-OH (25.86 mmol), 5.94 g of H-Phg-OiPr (25.86 mmol) and 3.49 g of HOBt in 100 ml of dimethylformamide. The mixture is left to stir at 0° C. for 1 hour and at room temperature for 4 hours. Subsequently, the mixture is left to stand overnight and the precipitate is then filtered off with suction and the filtrate concentrated. The residue is dissolved in ethyl acetate and the organic phase is extracted by shaking with a solution of potassium hydrogen sulphate (100 g of potassium sulphate and 50 g of potassium hydrogen sulphate dissolved in 1 liter of water), with a solution of sodium hydrogen carbonate and with water. It is then dried over anhydrous sodium sulphate and concentrated. The oily residue is chromatographed on silica gel using n-heptane/ethyl acetate (7:3).

Yield: 10.28 g (82%).

4g. $C_\beta$-Isopropyl L-aspartate-L-phenylglycine isopropyl ester hydrochloride 10.28 g of $C_\beta$-isopropyl (N-benzyloxycarbonyl)-L-aspartate-L-phenylglycine isopropyl ester (21.2 mmol) are dissolved in 250 ml of methanol and catalytically hydrogenated over Pd/active charcoal at a pH of 4.6 using an automated burette and adding 2 N methanolic HCl. The catalyst is filtered off with suction through kieselguhr and the filtrate is concentrated. The residue was taken up in water and freeze-dried.

Yield: 6.56 g of a white solid (80%).

4h. ((R,S)-4-(4-(Aminoiminomethyl)phenyl)-4-methyl-2,5-dioxoimidazolidin-1-yl)acetyl-L-aspartyl-L-phenylglycine diisopropyl ester hydrochloride 1.35 g of DCC (6.12 mmol) are added, at 0° C., to a solution of 2 g of ((R,S)-4-(4-(aminoiminomethyl) phenyl)-4-methyl-2,5-dioxoimidazolidin-1-yl)acetic acid hydrochloride (6.12 mmol), 2.37 g of H-Asp(OiPr)-Phg-OiPr hydrochloride (6.12 mmol) and 826.3 mg of HOBt in 15 ml of dimethylformamide. The mixture is left to stir at 0° C. for 1 hour and at room temperature for 5 hours. Subsequently, the mixture is left to stand in a cold room overnight, and the precipitate is then filtered off with suction and the filtrate concentrated. For purification, the substance is chromatographed on silica gel using methylene chloride/methanol/glacial acetic acid/water (8.5:1.5:0.15:0.15). The fractions containing the pure substance are concentrated. The residue is dissolved in water and freeze-dried.

Yield: 1.03 g of a white solid (27%).

$[a]_D = -9.3°$ (c=1, in methanol, 24° C.).

Example 5

((R,S)-4-(4-(Methoxycarbonylaminoiminomethyl) phenyl)-4-methyl-2,5-dioxoimidazolidin-1-yl)acetyl-L-aspartyl-L-phenylglycine diisopropyl ester 700 mg of ((R,S)-4-(4-(aminoiminomethyl)phenyl)-4-methyl-2,5-dioxoimidazolidin-1-yl)acetyl-L-aspartyl-L-phenylglycine diisopropyl ester hydrochloride (1.1 mmol; see Example 4) are dissolved in 15 ml of dimethylformamide and treated with 457.4 μl (3.3 mmol) of triethylamine and 212.6 μl of methyl chloroformate (2.75 mmol). The mixture is left to stir at room temperature for 8 hours and subsequently to stand at room temperature overnight. The reaction mixture is filtered and the filtrate is concentrated. The residue is taken up in a solution of sodium hydrogen carbonate and the aqueous phase is extracted three times by shaking with ethyl acetate. The organic phases are combined, dried over sodium sulphate and concentrated. For purification, the amorphous substance is chromatographed on silica gel using methylene chloride/methanol (20:1). The fractions containing the pure substance are concentrated. The oily residue is triturated with diethyl ether and the precipitate is filtered off with suction.

Yield: 410 mg of a white solid (55%).

Example 6

3-(((R,S)-4-(4-(Aminoiminomethyl)phenyl)-4-methyl-2,5-dioxoimidazolidin-1-yl)acetylamino)-2-benzyloxycarbonylaminopropionic acid 6a. tert-Butyl 3-amino-2-L-benzyloxycarbonylaminopropionate 5 g of 3-amino-2-L-benzyloxycarbonylaminopropionic acid (21 mmol); Bachem Chemie) are suspended in 50 ml of dioxane and treated, while being cooled, with 5 ml of concentrated sulphuric acid. The slightly yellowish solution is cooled with dry ice and 50 ml of condensed isobutylene are added to it. The mixture is shaken at room temperature for 3 days in an autoclave under nitrogen at a pressure of 20 atmospheres. Subsequently, excess isobutylene is driven out with a stream of nitrogen. The solution is adjusted to a pH of 10 with a 2 M solution of sodium carbonate (approximately 70 ml) and extracted three times by shaking with 200 ml of diethyl ether on each occasion. The organic phase is washed with water, dried over sodium sulphate and concentrated.

Yield: 4.31 g of oil (70%).

6b. tert-Butyl 3-(((R,S)-4-(4-(aminoiminomethyl)phenyl)-4-methyl-2,5-dioxoimidazolidin-1-yl)acetylamino)-2-benzyloxycarbonylaminopropionate hydrochloride 405 m of DCC (1.84 mmol) are added at 0° C., to a solution of 600 mg of ((R,S)-4-(4-(aminoiminomethyl) phenyl)-4-methyl-2,5-dioxoimidazolidin-1-yl)acetic acid hydrochloride (1.84 mmol; see Example 1), 542 mg of tert-butyl 3-amino-2-L-benzyloxycarbonylaminopropionate (1.84 mmol) and 249 mg of HOBt in 5 ml of dimethylformamide. The mixture is left to stir at 0° C. for 1 hour and at room temperature for 6 hours. Subsequently, the mixture is left to stand in a cold room overnight and the precipitate is then filtered off with suction and the filtrate concentrated. For purification, the substance is chromatographed on silica gel using methylene chloride/methanol/glacial acetic acid/water (8.5:1.5;0.15:0.15).

Yield: 680 mg of oil (still contains acetic acid).

6c. 3-(((R,S)-4-(4-(Aminoiminomethyl)phenyl)-4-methyl-2,5-dioxoimidazolidin-1-yl)acetylamino)-2-benzyloxycarbonylaminopropionic acid 670 mg of tert-butyl 3-(((R,S)-4-(4-(aminoiminomethyl)-phenyl)-4-methyl-2,5-dioxoimidazolidin-1-yl) acetylamino)-2-benzyloxycarbonylaminopropionate hydrochloride are dissolved in a mixture of 3.6 ml of trifluoroacetic acid, 0.4 ml of water and 0.4 ml of dimercaptoethane. After one hour at room temperature, the mixture is concentrated under a water suction vacuum. The residue is taken up in water and the aqueous phase is extracted three times with diethyl ether. The organic phase is washed once with water and the combined aqueous phases are freeze-dried. For purification, the substance is chromatographed on Sephadex LH20 using a mixture consisting of glacial acetic acid, n-butanol and water. The fractions containing the pure substance are concentrated. The residue is dissolved in water and freeze-dried.

Yield; 350 mg $[\alpha]_D = -12.4°$ (c=1, in methanol, 25°).

Example 7

2-Amino-3-(((R,S)-4-(4-(aminoiminomethyl) phenyl)-4-methyl-2,5-dioxoimidazolidin-1-yl) acetylamino)propionic acid hydrochloride 7a. tert-Butyl 2-amino-3-(((R,S)-4-(4-(aminoiminomethyl) phenyl)-4-methyl-2,5-dioxoimidazolidin-1-yl)acetylamino) propionate dihydrochloride 930 mg of tert-butyl 3-(((R,S)-4-(4-(aminoiminomethyl)-phenyl)-4-methyl-2,5-dioxoimidazolidin-1-yl) acetylamino)-2-benzyloxycarbonylaminopropionate hydrochloride (see Example 6b) are dissolved in 25 ml of methanol and hydrogenated catalytically over Pd/active charcoal at a pH of 4.6 using an automated burette and adding 2 N methanolic HCl. The catalyst is filtered off with suction through kieselguhr and the filtrate is freeze-dried. For purification, the substance is chromatographed on silica gel using methylene chloride/methanol/glacial acetic acid/water (9:4:0.3:0.65).

Yield: 300 mg of a white solid (42%).

7b. 2-Amino-3-(((R,S)-4-(4-(aminoiminomethyl)phenyl)-4-methyl-2,5-dioxoimidazolidin-1-yl)acetylamino)propionic acid hydrochloride 290 mg of tert-butyl 2-amino-3-(((R,S)-4-(4-(aminoimino-methyl)phenyl)-4-methyl-2,5-dioxoimidazolidin-1-yl) acetylamino)-propionate dihydrochloride are dissolved in a mixture of 3.6 ml of trifluoroacetic acid, 0.4 ml of water and 0.3 ml of dimercaptoethane. The solution is stirred at room temperature for one hour and then concentrated under a water suction vacuum. The residue is taken up in water and the aqueous phase is extracted three times with diethyl ether. The organic phase is washed once with water and the combined aqueous phases are freeze-dried. For purification, the substance is chromatographed on Sephadex LH20 using a mixture consisting of glacial acetic acid, n-butanol and water. The fractions containing the pure substance are concentrated. The residue is dissolved in water and freeze-dried.

Yield: 39 mg of a white solid (15%).

Example 8

((R,S)-4-(4-(Aminomethyl)phenyl)-4-methyl-2,5-dioxoimidazolidin-1-yl)acetyl-L-aspartyl-L-phenylglycine 8a. Methyl ((R,S)-4-(4-(aminomethyl)phenyl)-4-methyl-2,5-dioxoimidazolidin-1-yl)acetate acetate 1 g of methyl ((R,S)-4-(4-cyanophenyl)-4-methyl-2,5-dioxoimidazolidin-1-yl)acetate (3.48 mmol; see Example 1) is dissolved in a mixture consisting of 8 ml of ethanol and 2 ml of 50% acetic acid. 200 mg of 10% Pd/C are added to the solution which is then hydrogenated at room temperature for 2 hours in a shaking autoclave under a pressure of 3 bar. The catalyst is filtered off with suction through kieselguhr and the filtrate is concentrated. The oily residue is chromatographed on silica gel using methylene chloride/methanol (8:2).

Yield: 800 mg (79%).

8b. ((R,S)-4-(4-(Aminomethyl)phenyl)-4-methyl-2,5-dioxoimidazolidin-1-yl)acetic acid hydrochloride 750 mg of methyl ((R,S)-4-(4-(aminomethyl) phenyl)-4-methyl-2,5-dioxoimidazolidin-1-yl)acetate acetate (2.57 mmol) are dissolved in 15 ml of concentrated HCl. The solution is heated to boiling for 6 hours and is then concentrated. The residue is taken up in water and freeze-dried.

Yield: 700 mg (87%).

8c. ((R,S)-4-(4-(tert-Butoxycarbonylaminomethyl)phenyl)-4-methyl-2,5-dioxoimidazolidin-1-yl)acetic acid 300 mg of ((R,S)-4-(4-(aminomethyl)phenyl)-4-methyl-2,5-dioxoimidazolidin-1-yl)acetic acid hydrochloride (0.96 mmol) are dissolved in a mixture consisting of 2 ml of dioxane and 1 ml of water. The solution is adjusted to a pH of 8.0 with 1 N NaOH (approximately 1ml) and subsequently cooled down to 0° C. 230 mg of di-tert-butyl dicarbonate (1.05 mmol) are added while stirring. The reaction mixture is allowed to warm to room temperature and stirring is continued for a further 3 hours. During this period, the pH is maintained at a value of 8.0 by the continuous addition of 1 N NaOH (approximately 1.2 ml). The reaction mixture is concentrated in vacuo. The residue is adjusted, while being cooled (0° C.), to a pH of 2.0 with a solution of potassium hydrogen sulphate (100 g of potassium sulphate and 50 g of potassium hydrogen sulphate dissolved in 1 liter of water). The aqueous phase is extracted three times with ethyl acetate. The combined organic phases are extracted by being shaken with water and dried over anhydrous sodium sulphate. The organic phase is concentrated. The residue is taken up in a little water and freeze-dried.

Yield: 340 mg (94%).

8d. ((R,S)-4-4-(tert-Butoxycarbonylaminomethyl)phenyl)-4-methyl-2,5-dioxoimidazolidin-1-yl)acetyl-L-aspartyl-L-phenylglycine di-tert-butyl ester 104 µl of N-ethylmorpholine and 176 mg of DCC (0.9 mmol) are added, at 0° C., to a solution of 300 mg of ((R,S)-4-(4-(tert-butoxycarbonylaminomethyl)phenyl)-4-methyl-2,5-dioxoimidazolidin-1-yl) acetic acid (0.8 mmol), 332 mg of H-Asp (OBu$^t$)-Phg-OBu$^t$ hydrochloride (0.8 mmol) and 108 mg of HOBt in 3 ml of dimethylformamide. The mixture is left to stir at 0° C. for one hour and at room temperature for 4.5 hours. Subsequently the mixture is left to stand in a cold room overnight and the precipitate is then filtered off with suction and the filtrate is concentrated. For purification, the substance is chromatographed on silica gel using methylene chloride/methanol (20:1).

Yield: 320 mg of oil (54%).

8e. ((R,S)-4-(4-(Aminomethyl)phenyl)-4-methyl-2,5-dioxoimidazolidin-1-yl)acetyl-L-aspartyl-L-phenylglycine 270 mg of ((R,S)-4-(4-(tert-butoxycarbonylaminomethyl)-phenyl)-4-methyl-2,5-dioxoimidazolidin-1-yl)acetyl-L-aspartyl-L-phenylglycine di-tert-butyl ester (0.51 mmol) are dissolved in a mixture consisting of 1.8 ml of trifluoroacetic acid, 0.2 ml of water and 0.2 ml of dimercaptoethane. After one hour at room temperature, the mixture is concentrated under a water suction vacuum. For purification, the substance is chromatographed on Sephadex LH20 using a mixture consisting of glacial acetic acid, n-butanol and water. The fractions containing the pure substance are concentrated. The residue is dissolved in water and freeze-dried.

Yield: 160 mg (59%)

$[\alpha]_D$=+1.7° (c=1, in methanol, 23° C.).

Example 9

3-(((R,S)-4-(4-(Aminoiminomethyl)benzyl)-2,5-dioxoimidazolidin-1-yl)acetylamino)-2-benzyloxycarbonylaminopropionic acid 9a. tert-Butyl 3-(((R,S)-4-(4-(aminoiminomethyl) benzyl)-2,5-dioxoimidazolidin-1-yl)acetylamino)-2-benzyloxycarbonylaminopropionate 550 mg of DCC (2.7 mmol) are added, at 0° C., to a solution of 726 mg of (R,S)-4-(4-(aminoiminomethyl) benzyl-2,5-dioxoimidazolidin-1-yl)acetic acid hydrochloride (2.5 mmol; EP-A-0530505), 736 mg of tert-butyl 3-amino-2-L-benzyloxy-carbonylaminopropionate (2.5 mmol) and 338 mg of HOBt in 10 ml of dimethylformamide. Subsequently, the mixture is left to stir at 0° C. for one hour and at room temperature for 3 hours. The mixture is left to stand in a cold room overnight and the precipitate is then filtered off with suction and the filtrate is concentrated. The residue is triturated with a solution of sodium hydrogen carbonate and then with water. The remaining oil is dissolved in methanol and the insoluble residue (urea) is filtered off. The solution is concentrated.

Yield: 1.2 g (85%).

9b. 3-(((R,S)-4-(4-(Aminoiminomethyl)benzyl)-2,5-dioxoimidazolidin-1-yl)acetylamino)-2-benzyloxycarbonylaminopropionic acid 1.2 g of tert-butyl 3-(((R,S)-4-(4-(aminoiminomethyl)-benzyl)-2,5-dioxoimidazolidin-1-yl)acetylamino)-2-benzyloxycarbonylaminopropionate are dissolved in a mixture of 10.8 ml of trifluoroacetic acid and 0.8 ml of water. After one hour at room temperature, the solution is concentrated under a water suction vacuum. The residue is triturated with diethyl ether. The precipitate is filtered off with suction. For purification, the substance (380 mg) is chromatographed on Sephadex LH20 in a mixture consisting of glacial acetic acid, n-butanol and water. The fractions con taining the pure substance are concentrated. The residue is dissolved in water and freeze-dried.

Yield: 56 mg (5%).

Example 10

(R,S)-4-(4-Guanidinophenyl)-4-methyl-2,5-dioxoimidazolidin-1-yl)acetyl-L-aspartyl-L-phenylglycine 10a. ((R,S)-4-(4-Benzyloxycarbonylguanidinophenyl)-4-methyl-2,5-dioxoimidazolidin-1-yl)acetyl-L-aspartyl-L-phenylglycine di-tert-butyl ester 300 mg (0.625 mmol) of ((R,S)-4-(4-benzyloxycarbonylguanidinophenyl)-4-methyl-2,5-dioxoimidazolidin-1-yl)acetic acid (Ex. 11e) are dissolved in 50 ml of dimethylformamide, and 145 mg (0.7 mmol) of DCC and 85 mg (0.625 mmol) of HOBt are added at 0° C. The mixture is subsequently stirred for 1 hour and 260 mg (0.625 mmol) of H-Asp(OBu$^t$)-Phg-OBu$^t$ hydrochloride and 86.4 mg (0.75 mmol) of N-ethylmorpholine are then added. The mixture is stirred at room temperature for 4 hours and then concentrated and the residue dissolved in ethyl acetate; the precipitate is filtered off with suction and the organic phase is washed with a solution of sodium hydrogen carbonate and a solution of potassium hydrogen sulphate, dried and concentrated. The residue is stirred up with ether and filtered off with suction.

Yield: 370 mg (74%).

10b. ((R,S)-4-(4-Guanidinophenyl)-4-methyl-2,5-dioxoimidazolidin-1-yl)acetyl-L-aspartyl-L-phenylglycine 370 mg (0.46 mmol) of ((R,S)-4-(4-benzyloxycarbonylguanidinophenyl)-4-methyl-2,5-dioxoimidazolidin-1-yl) acetyl-L-aspartyl-L-phenylglycine di-tert-butyl ester are stirred at room temperature for 1 hour together with 3.7 ml of 90% trifluoroacetic acid and the solution is subsequently concentrated under high vacuum. The residue is dissolved in 50 ml of methanol and 50 mg of 10% Pd on charcoal are then added and the residue is hydrogenated at room temperature. Once the reaction is complete, the catalyst is filtered off and the mixture is concentrated and the residue is chromatographed, for purification, on Sephadex LH20 using a mixture consisting of glacial acetic acid, n-butanol and water. The fractions containing the pure substance are concentrated. The residue is dissolved in water and freeze-dried.

Yield: 123 mg (48%)

Melting point: 180° C.

Example 11

((R,S)-4-(4-Benzyloxycarbonylguanidinophenyl)-4-methyl-2,5-dioxoimidazolidin-1-yl)acetyl-L-aspartyl-L-phenylglycine dimethyl ester 11a. (R,S)-4-(4-Nitrophenyl)-4-methyl-2,5-dioxoimidazolidine 20.8 g (0.32 mol) of potassium cyanide and 96.1 g (1 mol) of ammonium carbonate are dissolved in 250 ml of water and carefully added to 49.5 g (0.3 mol) of 4-nitroacetophenone, dissolved in 250 ml of ethanol. The mixture is stirred at 50° C. for 5 hours and then cooled and the product which has precipitated out is filtered off with suction and subsequently washed with diethyl ether.

Yield: 56.2 g (80%)

Melting point: 237–240° C.

11b. Methyl ((R,S)-4-(4-nitrophenyl)-4-methyl-2,5-dioxoimidazolidin-1-yl)acetate 3.5 g (0.15 mol) of sodium are dissolved, under a nitrogen atmosphere, in 400 ml of methanol. 35.3 g (0.15 mol) of 4-((R,S)-4-nitrophenyl)-4-methyl-2,5-dioxoimidazolidine are then added and the mixture is heated under reflux for 2 hours. Following the addition of 24.9 g (0.15 mol) of potassium iodide and 16.3 g (0.15 mol) of methyl chloroacetate, the mixture is heated under reflux for a further 6 hours and then cooled and filtered with suction. The filtrate is concentrated and the residue is stirred up with tert-butyl methyl ether, filtered off with suction and dried.

Yield: 37.9 g (82%)

Melting point: 177–178° C.

11c. Methyl ((R,S)-4-(4-aminophenyl)-4-methyl-2,5-dioxoimidazolidin-1-yl)acetate 22.2 g (72.2 mmol) of methyl ((R,S)-4-(4-nitrophenyl)-4-methyl-2,5-dioxoimidazolidin-1-yl)acetate in 600 ml of ethanol are added carefully to a suspension consisting of 7.4 g of calcium chloride, 37 g of zinc dust, 11 ml of water and 7.4 ml of acetic acid. The mixture is heated under reflux for 4 hours. The hot mixture is filtered and the filtrate is concentrated and ethyl acetate and sodium hydrogen carbonate are added to the remaining residue. The organic phase is separated off and concentrated.

Yield: 12.2 g (61%).

11d. Methyl ((R,S)-4-(4-benzyloxycarbonylguanidinophenyl) -4-methyl-2,5-dioxoimidazolidin-1-yl)acetate 3.0 g (10.8 mmol) of methyl ((R,S)-4-(4-aminophenyl)-4-methyl-2,5-dioxoimidazolidin-1-yl)acetate and 2.4 g (10.8 mmol) of benzyloxycarbonyl-S-methylisothiourea are stirred at room temperature for 24 hours in 30 ml of methanol and 2.2 ml of acetic acid. After concentrating, the residue is dissolved in ethyl acetate and the organic phase is extracted with acidified water, washed until it becomes neutral, and concentrated. The residue is chromatographed on silica gel using ethyl acetate:methanol =9:1.

Yield: 2.85 g (58%)

11e. ((R,S)-4-(4-Benzyloxycarbonylguanidinophenyl)-4-methyl-2,5-dioxoimidazolidin-1-yl)acetic acid 2.81 g (6.2 mmol) of methyl ((R,S)-4-(4-benzyloxycarbonylguanidinophenyl)-4-methyl-2,5-dioxoimidazolidin-1-yl)-acetate are stirred at 85° C. for 3 hours together with 23 ml of water, 15 ml of 6 N hydrochloric acid and 60 ml of acetic acid. After concentrating, the residue is freeze-dried. For purification, the product is chromatographed on Sephadex LH20 using a homogeneous mixture of butanol/glacial acetic acid/water.

Yield: 850 mg (31%).

11f. ((R,S)-4-(4-Benzyloxycarbonylguanidinophenyl)-4-methyl-2,5-dioxoimidazolidin-1-yl)acetyl-L-aspartyl-L-phenylglycine dimethyl ester 500 mg (1.13 mmol) of ((R,S)-4-(4-benzyloxycarbonylguanidinophenyl)-4-methyl-2,5-dioxoimidazolidin-1-yl)acetic acid are dissolved in 30 ml of dimethylformamide. Once the solution has been cooled down to 0° C., 153 mg (1.13 mmol) of HOBt and 256 mg (1.24 mmol) of DCC are added. The mixture is stirred at 0° C. for 1 hour and 374 mg (1.13 mmol) of H-Asp(OMe)-Phg-OMe hydrochloride and 0.17 ml (1.36 mmol) of N-ethylmorpholine are then added and the mixture is subsequently stirred at room temperature overnight. The dicyclohexylurea which has precipitated out is filtered off and the filtrate is concentrated under high vacuum; the residue is dissolved in ethyl acetate and the organic phase is washed with a solution of sodium hydrogen carbonate and a solution of potassium hydrogen sulphate, dried and concentrated. The residue is chromatographed on silica gel using a mixture consisting of methylene chloride and methanol=9:1. The fractions containing the pure substance are concentrated and freeze-dried.

Yield: 620 mg (77%)

Example 12

Methyl (R,S)-3-(((R,S)-4-(4-(aminoiminomethyl) phenyl)-4-methyl-2,5-dioxoimidazolidin-1-yl) acetylamino)-3-phenylpropionate hydrochloride 440 mg of DCC (2 mmol) are added, at 0° C., to a solution of 653 mg of ((R,S)-4-(4-(aminoiminomethyl)phenyl)-4-methyl-2,5-dioxoimidazolidin-1-yl)acetic acid hydrochloride (2 mmol), 358 mg of methyl (R,S)-3-amino-3-phenylpropionate (2 mmol) and 270 mg of HOBt in 10 ml of dimethylformamide. The mixture is left to stir at 0° C. for one hour and at room temperature for 3 hours. Subsequently, the mixture is left to stand overnight and the precipitate is then filtered off with suction and the filtrate is concentrated. For purification, the substance (1.8 g) is chromatographed on Sephadex LH20 using a mixture consisting of glacial acetic acid, n-butanol and water. The fractions containing the pure substance are concentrated. The residue is dissolved in water and freeze-dried.

Yield: 597 mg (61%).

Example 13

(R,S)-3-(((R,S)-4-(4-(Aminoiminomethyl)phenyl)-4-methyl-2,5-dioxoimidazolidin-1-yl)acetylamino)-3-phenylpropionic acid hydrochloride 580 mg of methyl (R,S)-3-(((R,S)-4-(4-(aminoiminomethyl)-phenyl)-4-methyl-2,5-dioxoimidazolidin-1-yl) acetylamino)-3-phenylpropionate hydrochloride (1.19 mmol) are dissolved in 55 ml of concentrated hydrochloric acid and left to stand at room temperature for 5.5 hours. The solution is concentrated. For purification, the substance (540 mg) is chromatographed on Sephadex LH20 using a mixture consisting of glacial acetic acid, n-butanol and water. The fractions containing the pure substance are concentrated. The residue is dissolved in water and freeze-dried.

Yield: 477 mg (85%).

$[\alpha_D]$=+2.50° (c=1, in water, 23° C.).

Example 14

((R,S)-4-(4-Guanidinophenyl)-4-methyl-2,5-dioxoimidazolidin-1-yl)acetyl-L-aspartyl-L-phenylglycine dimethyl ester hydrochloride

Example 15

((R,S)-4-(4-Methoxycarbonylguanidinophenyl)-4-methyl-2,5-dioxoimidazolidin-1-yl)acetyl-L-aspartyl-L-phenylalanine diethyl ester

Example 16

$N_\alpha$-tert-Butyloxycarbonyl-$N_\beta$-(((R,S)-4-(4-guanidinophenyl)-4-methyl-2,5-dioxoimidazolidin-1-yl)acetyl)hydrazinoacetic acid

Example 17

Methyl $N_\alpha$-Benzyloxycarbonyl-$N_\beta$-(((R,S)-4-(4-benzyloxycarbonylguanidinophenyl)-4-methyl-2,5-dioxoimidazolidin-1-yl)acetyl)hydrazinoacetate

Example 18

$N_\beta$-tert-Butyloxycarbonyl-$N_\alpha$-(((R,S)-4-(4-benzyloxycarbonylguanidinophenyl)-4-methyl-2,5-dioxoimidazolidin-1-yl)acetyl)hydrazinoacetic acid

Example 19

(S)-2-tert-Butyloxycarbonylamino-6-((R,S)-4-(4-(aminoimino-methyl) phenyl)-4-methyl-2,5-dioxoimidazolidin-1-yl)hexanoic acid

Example 20

$N_\alpha$-((4-(4-(Aminoiminomethyl)benzylidene)-2,5-dioxoimidazolidin-1-yl)acetyl-$N_\beta$-(tert-butyloxycarbonyl)hydrazinoacetic acid The compounds of Examples 21 and 22 are diastereomers.

Example 21

((S or R)-4-(4-(Aminoiminomethyl)phenyl)-4-methyl-2,5-dioxoimidazolidin-1-yl)acetyl-L-aspartyl-L-phenylglycine Diastereomer I The diastereomeric mixture of ((R,S)-4-(4-(aminoiminomethyl phenyl)-4-methyl-2,5-dioxoimidazolidin-1-yl) acetyl-L-aspartyl-L-phenylglycine (Example 1) is resolved by chromatography on a LiChroprep-RP-18 reversed-phase column (10 μm) using a water/acetonitrile mixture (880 ml of water; 120 ml of acetonitrile; 1 ml of trifluoroacetic acid) as the eluent. Fractions which contain the peak which elutes first from the column are concentrated. The residue is taken up in a little water and freeze-dried.

$[\alpha]_D$=−14° (c=1, in water, 30° C.).

FAB MS: 539 (M+H)$^+$

Example 22

((R or S)-4-(4-(Aminoiminomethyl)phenyl)-4-methyl-2,5-dioxoimidazolidin-1-yl)acetyl-L-aspartyl-L-phenylglycine Diastereomer II In analogy with Example 21, the diastereomer II is isolated from the diastereomeric mixture of ((R,S)-4-(4-(aminoimino-methyl) phenyl)-4-methyl-2,5-dioxoimidazolidin-1-yl) acetyl-L-aspartyl-L-phenylglycine by chromatography on a LiChroprep-RP-18 reversed-phase column (10 μm). For this, the fractions are concentrated which contain the second peak eluting from the column. The residue is taken up in a little water and freeze-dried.

$[\alpha]_D$=+20° (c=1, in water, 30° C.).

FAB MS: 539 (M+H)$^+$

Example 23

((R,S)-4-(4-(Aminoiminomethyl)phenyl)-4-methyl-2,5-dioxoimidazolidin-1-yl)acetyl-L-aspartyl-L-phenylglycine methyl ester

FAB MS: 553 (M+H)$^+$

Example 24

((R,S)-4-(4-(Aminoiminomethyl)phenyl)-3-ethyl-4-methyl-2,5-dioxoimidazolidin-1-yl)acetyl-L-aspartyl-L-phenylglycine

FAB MS: 466 (M+H)$^+$

Example 25

((R,S)-4-(4-(Aminoiminomethyl)phenyl)-3-benzyl-4-methyl-2,5-dioxoimidazolidin-1-yl)acetyl-L-aspartyl-L-phenylglycine

FAB MS: 629 (M+H)$^+$

Example 26

((R,S)-4-(4-(Aminoiminomethyl)phenyl)-4-cyclopropyl-2,5-dioxoimidazolidin-1-yl)acetyl-L-aspartyl-L-phenylglycine 26a. 4-Cyanophenylcyclopropylmethanone 22.5 g of 4-bromophenylcyclopropylmethanone (100 mmol) and 10.3 g of CuCN (100 mmol) are dissolved in 15 ml of DMF and heated under reflux, with stirring, for 4 hours. The suspension is allowed to cool down to 70° C. and is then poured into a solution consisting of 40 g of iron(III)

chloride, 10 ml of conc. HCl and 60 ml of water. The mixture is stirred at 70° C. for 20 minutes. It is then extracted three times with 90 ml of toluene on each occasion. The combined organic phases are washed with 250 ml of 2N hydrochloric acid and with 250 ml of 2N sodium hydroxide solution, and then concentrated. The solid residue is triturated with petroleum ether and filtered off with suction.

Yield: 14.57 g (85%)
FAB MS: 172 (M+H)$^+$ 26b. ((R,S)-4-(4-(Aminoiminomethyl)phenyl)-4-cyclopropyl-2,5-dioxoimidazolidin-1-yl)acetyl-L-aspartyl-L-phenylglycine The synthesis is carried out in analogy with Example 1 proceeding from 4-cyanophenylcyclopropylmethanone.
FAB MS: 565 (M+H)$^+$

Example 27

((R,S)-4-(4-(Aminoiminomethyl)phenyl)-4-ethyl-2,5-dioxoimidazolidin-1-yl) acetyl-L-aspartyl-L-phenylglycine The synthesis is carried out in analogy with Example 26 proceeding from 1-(4-bromophenyl)-1-propanone.
FAB MS: 553 (M+H)$^+$

Example 28

((R,S)-4-(4-(Aminoiminomethyl)phenyl)-4-benzyl-2,5-dioxoimidazolidin-1-yl) acetyl-L-aspartyl-L-phenylglycine The synthesis is carried out in analogy with Example 26 proceeding from 2-phenyl-1-(4-bromophenyl)-1-ethanone.
FAB MS: 615 (M+H)$^+$

Example 29

((R,S)-4-(4-(Aminoiminomethyl)phenyl)-4-tert-butyl-2,5-dioxoimidazolidin-1-yl) acetyl-L-aspartyl-L-phenylglycine 29a. 4-Bromophenyl-tert-butylmethanone 21 g of freshly powdered, anhydrous potassium hydroxide (375 mmol) are overlaid with 50 ml of anhydrous toluene. 20 mg of 18-crown-6 (0.75 mmol) and 9.95 g of 4-bromoacetophenone (50 mmol) are added. The mixture is heated to 70° C. 24.94 ml of iodomethane (395 mmol) are added slowly to the reaction solution which is then stirred at 70° C. for 3.5 hours. The organic phase is extracted with water. The aqueous phase is extracted twice with diethyl ether. The organic phases are combined, dried over sodium sulphate and concentrated. The crude product (11.46 g) is alkylated once more by the above procedure since the reaction has still not gone to completion. The resulting product (10.86 g) is purified by means of high vacuum distillation using a silvered jacketed column.

Yield: 3.9 g (32%)
FAB MS: 242 (M+H)$^+$ 29b. ((R,S)-4-(4-(Aminoiminomethyl)phenyl)-4-tert-butyl-2,5-dioxoimidazolidin-1-yl)acetyl-L-aspartyl-L-phenylglycine The synthesis is carried out in analogy with Example 26 proceeding from 4-bromophenyl-tert-butylmethanone.
FAB MS: 581 (M+H)$^+$

Example 30

(R,S)-3-(((R,S)-4-(4-(Aminoiminomethyl)phenyl)-4-methyl-2,5-dioxoimidazolidin-1-yl)acetylamino)-2-pentylcarbonylaminopropionic acid

FAB MS; 475 (M+H)$^+$

Example 31

(R,S)-3-(((R,S)-4-(4-(Aminoiminomethyl)phenyl)-3,4-dimethyl-2,5-dioxoimidazolidin-1-yl)acetylamino)-2-pentylcarbonylaminopropionic acid

FAB MS: 489 (M+H)$^+$

Example 32

(R,S)-3-(((R,S)-4-(4-(Aminoiminomethyl)phenyl)-4-methyl-2,5-dioxoimixidazolidin-1-yl) acetylamino)-2-butylsulphonylaminopropionic acid

FAB MS: 497 (M+H)$^+$

Example 33

(R,S)-3-(((R,S)-4-(4-(Aminoiminomethyl)phenyl)-3,4-dimethyl-2,5-dioxoimidazolidin-1-yl) acetylamino)-2-butylsulphonylaminopropionic acid

FAB MS: 511 (M+H)$^+$

Example 34

2-((R,S)-4-(4-(Aminoiminomethyl)phenyl)-4-methyl-2,5-dioxoimidazolidin-1-yl)-N-((R,S)-1-benzyloxycarbonyl-2-(3-phenylureidosulphonyl)ethyl)acetamide

FAB MS: 650 (M+H)$^+$

Example 35

(R,S)-3-(((R,S)-4-(4-(Aminoiminomethyl)phenyl)-4-methyl-2,5-dioxoimidazolidin-1-yl) acetylamino)-3-(3-hydroxy-4-methoxy-phenyl)propionic acid

FAB MS: 484 (M+H)$^+$

Example 36

(R,S)-3-(((R,S)-4-(4-(Aminoiminomethyl)phenyl)-4-methyl-2,5-dioxoimidazolidin-1-yl)acetylamino)-3-(4-hydroxy-3-methoxy-phenyl)propionic acid

FAB MS: 484 (M+H)$^+$

Example 37

(R,S)-3-(((R,S)-4-(4-(Aminoiminomethyl)phenyl)-4-methyl-2,5-dioxoimidazolidin-1-yl)acetylamino)-3-(4-ethoxyphenyl)propionic acid

FAB MS: 482 (M+H)$^+$

Example 38

(R,S)-3-(((R,S)-4-(4-(Aminoiminomethyl)phenyl)-4-methyl-2,5-dioxoimidazolidin-1-yl)acetylamino)-3-(1-naphthyl)propionic acid

FAB MS: 488 (M+H)$^+$

Example 39

(R,S)-3-(((R,S)-4-(4-(Aminoiminomethyl)phenyl)-4-methyl-2,5-dioxomidazolidin-1-yl)acetylamino)-3-(3-nitrophenyl)propionic acid

FAB MS: 483 (M+H)$^+$

Example 40

(R,S)-3-(((R,S)-4-(4-(Aminoiminomethyl)phenyl)-4-methyl-2,5-dioxoimidazolidin-1-yl)acetylamino)-3-(4-hydroxycarbonylphenyl)propionic acid

FAB MS: 482 (M+H)$^+$

Example 41

(R,S)-3-(((R,S)-4-(4-(Aminoiminomethyl)phenyl)-4-methyl-2,5-dioxoimidazolidin-1-yl)acetylamino)-3-(3-benzyloxyphenyl)propionic acid

FAB MS: 544 (M+H)$^+$

Example 42

(R,S)-3-(((R,S)-4-(4-(Aminoiminomethyl)phenyl)-4-methyl-2,5-dioxoimidazolidin-1-yl)acetylamino)-3-(3-hydroxycarbonylphenyl)propionic acid

FAB MS: 482 (M+H)$^+$

Example 43

(R,S)-3-(((R,S)-4-(4-(Aminoiminomethyl)phenyl)-4-methyl-2,5-dioxoimidazolidin-1-yl)acetylamino)-3-(3-phenoxyphenyl)propionic acid

FAB MS: 530 (M+H)$^+$

Example 44

(R,S)-3-(((R,S)-4-(4-(Aminoiminomethyl)phenyl)-4-methyl-2,5-dioxoimidazolidin-1-yl)acetylamino)-3-(3,4,5-trimethoxyphenyl)propionic acid

FAB MS: 528 (M+H)$^+$

Example 45

(R,S)-3-(((R,S)-4-(4-(Aminoiminomethyl)phenyl)-4-methyl-2,5-dioxoimidazolidin-1-yl)acetylamino)-3-(4-hydroxyphenyl)propionic acid

FAB MS: 454 (M+H)$^+$

Example 46

(R,S)-3-(((R,S)-4-(4-(Aminoiminomethyl)phenyl)-4-methyl-2,5-dioxoimidazolidin-1-yl)acetylamino)-3-(4-phenylphenyl)propionic acid

FAB MS: 514 (M+H)$^+$

Example 47

(R,S)-3-(((R,S)-4-(4-(Aminoiminomethyl)phenyl)-4-methyl-2,5-dioxoimidazolidin-1-yl)acetylamino)-3-(3-pyridyl)propionic acid

FAB MS: 439 (M+H)$^+$

Example 48

(R,S)-3-(((R,S)-4-(4-(Aminoiminomethyl)phenyl)-4-methyl-2,5-dioxoimidazolidin-1-yl)acetylamino) butyric acid

FAB MS: 376 (M+H)$^+$

Example 49

(R,S)-3-(((R,S)-4-(4-(Aminoiminomethyl)phenyl)-4-methyl-2,5-dioxoimidazolidin-1-yl)acetylamino)-3-cyclohexylpropionic acid

FAB MS: 444 (M+H)$^+$

Example 50

(R,S)-3-(((R,S)-4-(4-(Aminoiminomethyl)phenyl)-3,4-dimethyl-2,5-dioxoimidazolidin-1-yl)acetylamino)-3-phenylpropionic acid

FAB MS: 452 (M+H)$^+$

Example 51

Ethyl (R,S)-3-(((R,S)-4-(4-(Aminoiminomethyl)phenyl)-3,4-dimethyl-2,5-dioxomidazolidin-1-yl)acetylamino)-3-phenylpropionate hydrochloride

FAB MS: 480 (M+H)$^+$

Example 52

(R,S)-3-(((R,S)-4-(4-(Aminoiminomethyl)phenyl)-3-ethyl-4-methyl-2,5-dioxoimidazolidin-1-yl)acetylamino)-3-phenylpropionic acid

FAB MS: 466 (M+E)$^+$

Example 53

Ethyl (R,S)-3-(((R,S)-4-(4-(aminoiminomethyl)phenyl)-3-ethyl-4-methyl-2,5-dioxoimidazolidin-1-yl)acetylamino)-3-phenylpropionate hydrochloride

FAB MS: 494 (M+H)$^+$

Example 54

Ethyl (R,S)-3-(((R,S)-4-(4-(Aminoiminomethyl)phenyl)-4-methyl-2,5-dioxoimidazolidin-1-yl)acetylamino)-3-phenylpropionate hydrochloride

FAB MS: 466 (M+H)$^+$

Example 55

Ethyl (S)-3-(((R or S)-4-(4-(aminoiminomethyl)phenyl)-4-methyl-2,5-dioxoimidazolidin-1-yl)acetylamino)-3-phenylpropionate hydrochloride The compound is derived from the diastereomer II of Example 58.

340 mg of (S)-3-(((R or S)-4-(4-(aminoiminomethyl)-phenyl)-4-methyl-2,5-dioxoimidazolidin-1-yl)acetylamino)-3-phenylpropionic acid (0.78 mmol) (Example 58) are dissolved in 60 ml of a 2N ethanolic solution of HCl and left to stand at room temperature for 2 hours. The solution is concentrated and the residue is dissolved in water. This solution is filtered and freeze-dried.

Yield: 375 mg of a white solid (96%).

$[\alpha]_D = -55.51°$ (c=1, in water, 21° C.).

FAB MS: 466 (M+H)$^+$

Example 56

(S)-3-(((R,S)-4-(4-(aminoiminomethyl)phenyl)-4-methyl-2,5-dioxoimidazolidin-1-yl)acetylamino)-3-phenylpropionic acid hydrochloride 12.37 g of ethyl (S)-3-(((R,S)-4-(4-(aminoiminomethyl)-phenyl)-4-methyl-2,5-dioxoimidazolidin-1-yl) acetylamino-3-phenyl-propionate hydrochloride (26.6 mmol) (Example 71) are dissolved in 200 ml of concentrated hydrochloric acid and left to stand at room temperature for 7.5 hours. The solution is concentrated. 200 ml of concentrated hydrochloric acid are added to the residue and this solution is left to stand at room temperature for 7.5 hours and then concentrated. 11.6 g of crude product are obtained.

For purification, a part of the substance (255 mg) is chromatographed on Sephadex LH20 in a mixture consisting of glacial acetic acid, n-butanol and water. The fractions containing the pure substance are concentrated. The residue is dissolved in water and freeze-dried.

Yield: 232 mg.
FAB MS: 438 (M+H)$^+$

Example 57

Diastereomer I (S)-3-(((S or R)-4-(4-(Aminoiminomethyl)phenyl)-4-methyl-2,5-dioxoimidazolidin-1-yl)acetylamino)-3-phenylpropionic acid The diastereomeric mixture of (S)-3-(((R,S)-4-(4-(aminoiminomethyl)phenyl)-4-methyl-2,5-dioxoimidazolidin-1-yl) acetylamino)-3-phenylpropionic acid hydrochloride (Example 56) is resolved by chromatography on a LiChroprep RP-18 reversed-phase column (10 μm) using a water/acetonitrile mixture (920 ml of water; 80 ml of acetonitrile; 1 g of ammonium acetate) as the eluent. For this purpose, 500 mg of the diastereomeric mixture are in each case loaded onto a column having a charging volume of 450 ml. Fractions containing the peak eluting first from the column are concentrated. The ammonium acetate is removed by freeze-drying three times.

Yield per column run: 245 mg (49%)
$[\alpha]_D$=−110.4° (c=1, in water, 30° C.)
FAB MS: 438 (M+H)$^+$

Example 58

Diastereomer II (S)-3-(((R or S)-4-(4-(Aminoiminomethyl)phenyl)-4-methyl-2,5-dioxoimidazolidin-1-yl)acetylamino)-3-phenylpropionic acid In analogy with Example 57, the diastereomer II is isolated from the diastereomeric mixture of (S)-3-(((R,S)-4-(4-(aminoiminomethyl)phenyl)-4-methyl-2,5-dioxoimidazolidin-1-yl)-acetylamino)-3-phenylpropionic acid hydrochloride (Example 56) by chromatography on a LiChroprep-RP-18 reversed-phase column (10 μm). For this purpose, the fractions are concentrated which contain the second peak eluting from the column. The ammonium acetate is removed by freeze-drying three times.

Yield per column run: 200 mg (40%)
$[\alpha]_D$=−62.8° (c=1, in water, 30° C.)
FAB MS: 438 (M+H)$^+$

Example 59

Diastereomer III (R)-3-(((S or R)-4-(4-(aminoiminomethyl)phenyl)-4-methyl-2,5-dioxoimidazolidin-1-yl)acetylamino)-3-phenylpropionic acid 145 mg of the diastereomeric mixture of (R)-3-(((R,S)-4-(4-(aminoiminomethyl)phenyl)-4-methyl-2,5-dioxoimidazolin-1-yl)acetylamino)-3-phenylpropionic acid hydrochloride (Example 61) are resolved by chromatography on a LiChroprep-RP-18 reversed-phase column (10 μm) in analogy with Example 57. Fractions which contain the first peak eluting from the column are concentrated. The ammonium acetate is removed by freeze-drying three times.

Yield: 60 mg (41%).
$[\alpha]_D$=+92.7° (c=1, in water, 30° C.)
FAB MS: 438 (M+H)$^+$

Example 60

Diastereomer IV (R)-3-(((R or S)-4-(4-(aminoiminomethyl)phenyl)-4-methyl-2,5-dioxoimidazolidin-1-yl)acetylamino)-3-phenylpropionic acid In analogy with Example 59, the diastereomer IV is isolated from the diastereomeric mixture of (R)-3-(((R,S)-4-(4-(aminoiminomethyl)phenyl)-4-methyl-2,5-dioxoimidazolidin-1-yl)-acetylamino)-3-phenylpropionic acid hydrochloride (Example 61)by chromatography on a LiChroprep-RP-18 reversed-phase column (10 μm). For this purpose, the fractions are concentrated which contain the second peak eluting from the column. The ammonium acetate is removed by freeze-drying three times.

Yield: 63 mg (43%).
$[\alpha]_D$=+51.4° (c=1, in water, 30° C.)
FAB MS: 438 (M+H)$^+$

Example 61

(R)-3-(((R,S)-4-(4-(aminoiminomethyl)phenyl)-4-methyl-2,5-dioxoimidazolidin-1-yl)acetylamino)-3-phenylpropionic acid hydrochloride The substance is prepared in analogy with Examples 71 and 56. In this case, the synthesis proceeds from (S)-phenylglycine.

FAB MS: 438 (M+H)$^+$

Example 62

The compound is derived from the diastereomer I of Example 57.

Ethyl (S)-3-(((S or R)-4-(4-(aminoiminomethyl)phenyl)-4-methyl-2,5-dioxoimidazolidin-1-yl)acetylamino)-3-phenylpropionate hydrochloride

FAB MS: 466 (M+H)$^+$

Example 63

The compound is derived from the diastereomer II of Example 58.

Methyl (S)-3-(((R or S)-4-(4-(aminoiminomethyl)phenyl)-4-methyl-2,5-dioxoimidazolidin-1-yl)acetylamino)-3-phenylpropionate hydrochloride

FAB MS: 452 (M+H)$^+$

Example 64

The compound is derived from the diastereomer II of Example 58.

Isopropyl (S)-3-(((R or S)-4-(4-(aminoiminomethyl)phenyl)-4-methyl-2,5-dioxoimidazolidin-1-yl)acetylamino)-3-phenylpropionate hydrochloride

FAB MS: 480 (M+H)$^+$

Example 65

(R,S)-3-(((R,S)-4-(4-aminoiminomethyl)phenyl)-4-methyl-2,5-dioxoimidazolidin-1-yl)acetyl-(N-methylamino))-3-(3-pyridyl)propionic acid

FAB MS: 453 (M+H)$^+$

Example 66

(R,S)-3-(((R,S)-4-(4-(aminoiminomethyl)phenyl)-4-methyl-2,5-dioxoimidazolidin-1-yl)acetyl-(N-methylamino))-3-phenylpropionic acid

FAB MS: 452 (M+H)$^+$

Example 67

(R,S)-3-(((R,S)-4-(4-(aminoiminomethyl)phenyl)-4-methyl-2,5-dioxoimidazolidin-1-yl)acetylamino)-3-(3,4-methylenedioxyphenyl)propionic acid

FAB MS: 482 (M+H)$^+$

Example 68

(2-((R,S)-4-(4-(aminoiminomethyl)phenyl)-4-methyl-2,5-dioxoimidazolidin-1-yl)acetyl)-L-aspartyl-1-adamantylamide

68a. (N-Benzyloxycarbonyl)-L-aspartic acid-$C_\beta$-tert-butyl ester-1-adamantylamide 1.69 ml of N-ethylmorpholine (13 mmol) and 2.86 g of DCC (13 mmol) are added, at 0° C., to a suspension of 4.2 g of Z-L-Asp (OBu$^t$)-OH (13 mmol), 1.97 g of 1-aminoadamantane (13 mmol) and 1.76 g of HOBt (13 mmol) in 140 ml of dimethylformamide. The mixture is left to stir at 0° C. for 1 hour and at room temperature for 3 hours. Subsequently, the mixture is left to stand overnight and the precipitate is then filtered off with suction and the filtrate is concentrated. The residue is taken up in a solution of sodium hydrogen carbonate and the aqueous phase is extracted by shaking with ethyl acetate. The organic phase is extracted by shaking with a solution of potassium hydrogen sulphate (100 g of potassium sulphate and 50 g of potassium hydrogen sulphate dissolved in 1 liter of water), with a solution of sodium hydrogen carbonate and with water. It is dried over anhydrous sodium sulphate and concentrated.

Yield: 6.21 g (crude product).

68b. L-Aspartic acid-$C_\beta$-tert-butyl ester-1-adamantylamide hydrochloride.

6.21 g of (N-benzyloxycarbonyl)-L-aspartic acid-$C_\beta$-tert-butyl ester-1-adamantylamide (crude product) are dissolved in 50 ml of methanol and catalytically hydrogenated over Pd/active charcoal at a pH of 4.6 using an automated burette and adding 2N methanolic HCl. The catalyst is filtered off with suction through kieselguhr and the filtrate is concentrated. The residue is triturated with diethyl ether, filtered off with suction and dried.

Yield: 4 g (85% based on quantity of Z-L-Asp(OBu$^t$)-OH employed);

FAB MS (M+H)$^+$=323.

68c. (2-((R,S)-4-(4-(Aminoiminomethyl)phenyl)-4-methyl-2,5-dioxoimidazolidin-1-yl)acetyl)-L-aspartyl-$C_\beta$-tert-butyl ester-1-adamantylamide hydrochloride 0.26 ml of N-ethylmorpholine (2 mmol) and 440 mg of DCC (2 mmol) are added, at 0° C., to a suspension of 654 mg of 2-((R,S)-4-(4-(aminoiminomethyl)phenyl)-4-methyl-2,5-dioxoimidazolidin-1-yl)acetic acid hydrochloride (2 mmol; see Example 1), 718 mg of L-aspartic acid-$C_\beta$-tert-butyl ester-1-adamantylamide hydrochloride (2 mmol) and 270 mg of HOBt (2 mmol) in 20 ml of dimethylformamide. The mixture is left to stir at 0° C. for 1 hour and at room temperature for 3 hours. Subsequently, the mixture is left to stand at room temperature overnight and the precipitate is then filtered off with suction and the filtrate is concentrated. The residue is taken up in a solution of sodium hydrogen carbonate and the aqueous phase is extracted by shaking with pentanol. The organic phase is extracted by shaking with a solution of potassium hydrogen sulphate and with water. It is dried over anhydrous sodium sulphate and concentrated. The residue is triturated with diethyl ether, filtered off with suction and dried.

Yield: 1.35 g (crude product).

68d. (2-((R,S)-4-(4-Aminoiminomethyl)phenyl)-4-methyl-2,5-dioxoimidazolidin-1-yl)acetyl)-L-aspartyl-1-adamantylamide.

1.35 g of (2-((R,S)-4-(4-(Aminoiminomethyl) phenyl)-4-methyl-2,5-dioxoimidazolidin-1-yl)acetyl)-L-aspartyl-$C_\beta$-tert-butyl ester-1-adamantylamide hydrochloride are dissolved in a mixture of 12.15 ml of trifluoroacetic acid, 1.35 ml of water and 1.35 ml of dimercaptoethane. After 1 hour at room temperature, the mixture is concentrated under a water suction vacuum. The residue is triturated with diethyl ether, filtered off with suction and dried. For purification, the substance is chromatographed on Sephadex LH20 in a mixture consisting of glacial acetic acid, n-butanol and water. The fractions containing the pure substance are concentrated. The residue is dissolved in water in the presence of a little acetic acid and freeze-dried.

Yield: 1.02 g; FAB MS (M+H)$^+$=539

Example 69

(2-((R,S)-4-(4-(Aminoiminomethyl)phenyl)-4-methyl-2,5-dioxoimidazolidin-1-yl)acetyl)-L-aspartyl-2-adamantylamide

69a. (N-benzyloxycarbonyl)-L-aspartic acid-$C_\beta$-tert-butyl ester-2-adamantylamide 1.69 ml of N-ethylmorpholine (13 mmol) and 2.86 g of DCC (13 mmol) are added, at 0° C., to a suspension of 4.2 g of Z-L-Asp (OBu$^t$)-OH (13 mmol), 2.44 g of 2-aminoadamantane hydrochloride (13 mmol) and 1.76 g of HOBt (13 mmol) in 40 ml of dimethylformamide. The mixture is left to stir at 0° C. for 1 hour and at room temperature for 3 hours. Subsequently, the mixture is left to stand overnight and the precipitate is then filtered off with suction and the filtrate is concentrated. The residue is taken up in a solution of sodium hydrogen carbonate and the aqueous phase is extracted by shaking with ethyl acetate. The organic phase is extracted by shaking with a solution of potassium hydrogen sulphate, with a solution of sodium hydrogen carbonate, and with water. It is dried over anhydrous sodium sulphate and concentrated.

Yield: 6.32 g (crude product).

69b. L-Aspartic acid-$C_\beta$-tert-butyl ester-2-adamantylamide hydrochloride 6.32 g of (N-benzyloxycarbonyl)-L-aspartic acid-$C_\beta$-tert-butyl ester-2-adamantylamide (crude product) are dissolved in 50 ml of methanol and catalytically hydrogenated over Pd/active charcoal at a pH of 4.6 using an automated burette and adding 2N methanolic HCl. The catalyst is filtered off with suction through kieselguhr and the filtrate is concentrated. The residue is dissolved in diethyl ether and concentrated. An amorphous solid is obtained.

Yield: 4 g (85% based on quantity of Z-L-Asp(OBu$^t$)-OH employed);

FAB MS (M+H)$^+$=323

69c. (2-((R,S)-4-(4-(Aminoiminomethyl)phenyl)-4-methyl-2,5-dioxoimidazolidin-1-yl)acetyl)-L-aspartyl-$C_\beta$-tert-butyl ester-2-adamantylamide hydrochloride 0.26 ml of N-ethylmorpholine (2 mmol) and 440 mg of DCC (2 mmol) are added, at 0° C., to a suspension of 654 mg of 2-((R,S)-4-(4-(aminoiminomethyl)phenyl)-4-methyl-2,5-dioxoimidazolidin-1-yl)acetic acid hydrochloride (2 mmol; see Example 1), 718 mg of L-aspartic acid-$C_\beta$-tert-butyl ester-2-adamantylamide hydrochloride (2 mmol) and 270 mg of HOBt (2 mmol) in 20 ml of dimethyl formamide. The mixture is left to stir at 0° C. for 1 hour and at room temperature for 2 hours. Subsequently, the mixture is left to stand at room temperature overnight and the precipitate is then filtered off with suction and the filtrate is concentrated. The residue is taken up in a solution of sodium hydrogen carbonate and the aqueous phase is extracted by shaking with pentanol. The organic phase is extracted by shaking with a solution of potassium hydrogen sulphate and with water. It is dried over anhydrous sodium sulphate and concentrated. The residue is triturated with diethyl ether, filtered off with suction and dried.

Yield: 1.27 g (crude product).

69d. (2-((R,S)-4-(4-(Aminoiminomethyl)-phenyl)-4-methyl-2,5-dioxoimidazolidin-1-yl)acetyl)-L-aspartyl-2-adamantylamide 1.27 g (2-((R,S)-4-(4-Aminoiminomethyl)phenyl)-4-methyl-2,5-dioxoimidazolidin-1-yl)acetyl)-L-aspartyl-$C_\beta$-tert-butyl ester-2-adamantylamide hydrochloride are dissolved in a mixture of 11.43 ml of trifluoroacetic acid, 1.27 ml of water and 1.27 ml of dimercaptoethane. After 1 hour at room temperature, the mixture is concentrated under a water suction vacuum. The residue is triturated with diethyl ether, filtered off with suction and dried. For purification, the substance is chromatographed on Sephadex LH20 in a mixture consisting of glacial acetic acid, n-butanol and water. The fractions containing the pure substance are concentrated. The residue is dissolved in water in the presence of a little acetic acid and freeze-dried.

Yield: 615.8 mg; FAB MS $(M+H)^+=539$

Example 70

(2-((R,S)-4-(4-(Aminoiminomethyl)phenyl)-4-methyl-2,5-dioxoimidazolidin-1-yl)acetyl)-L-aspartyl-(1-adamantylmethyl) amide.

70a. (N-Benzyloxycarbonyl)-L-aspartic acid-$C_\beta$-tert-butyl ester-(1-adamantylmethyl)amide 2.66 g of DCC (12.1 mmol) are added, at 0° C., to a suspension of 3.91 g of Z-L-Asp(OBu$^t$)-OH (12.1 mmol), 2 g of 1-aminomethyladamantane (12.1 mmol) and 1.63 g of HOBt (12.1 mmol) in 60 ml of dimethylformamide. The mixture is left to stir at 0° C. for 1 hour and at room temperature for 2 hours. Subsequently, the mixture is left to stand overnight and the precipitate is then filtered off with suction and the filtrate is concentrated. The residue is taken up in a solution of sodium hydrogen carbonate and the aqueous phase is extracted by shaking with ethyl acetate. The organic phase is extracted by shaking with a solution of potassium hydrogen sulphate, with a solution of sodium bicarbonate and with water. It is dried over anhydrous sodium sulphate and concentrated.

Yield: 6 g (crude product).

70b. L-Aspartic acid-$C_\beta$-tert-butyl ester-(1-adamantylmethyl)amide hydrochloride 6 g of (N-benzyloxycarbonyl)-L-aspartic acid-$C_\beta$-tert-butyl ester-(1-adamantylmethyl)amide (crude product) are dissolved in 50 ml of methanol and hydrogenated catalytically over Pd/active charcoal at a pH of 4.6 using an automated burette and while adding 2N methanolic HCl. The catalyst is filtered off with suction through kieselguhr and the filtrate is concentrated. The residue is triturated with diethyl ether, filtered off with suction and dried.

Yield: 3.85 g (85% based on the quantity of Z-L-Asp (OBu$^t$)-OH employed); FAB MS $(M+H)^+=337$.

70c. (2-((R,S)-4-(4-(aminoiminomethyl)phenyl)-4-methyl-2,5-dioxoimidazolidin-1-yl)acetyl-L-aspartyl-$C_\beta$-tert-butyl ester-(1-adamantylmethyl)amide hydrochloride 0.26 ml of N-ethylmorpholine (2 mmol) and 440 mg of DCC (2 mmol) are added, at 0° C., to a suspension of 654 mg of 2-((R,S)-4-(4-(aminoiminomethyl)phenyl)-4-methyl-2,5-dioxoimidazolidin-1-yl)acetic hydrochloride (2 mmol; see Example 1), 746 mg of L-aspartic acid-$C_\beta$-tert-butyl ester-(1-adamantylmethyl)amide hydrochloride (2 mmol) and 270 mg of HOBt (2 mmol) in 20 ml of dimethylformamide. The mixture is left to stir at 0° C. for 1 hour and at room temperature for 3 hours. Subsequently, the mixture is left to stand at room temperature overnight and the precipitate is then filtered off with suction and the filtrate is concentrated. The residue is taken up in a solution of sodium hydrogen carbonate and the aqueous phase is extracted by shaking with pentanol. The organic phase is extracted by shaking with a solution of potassium hydrogen sulphate and with water. It is dried over anhydrous sodium sulphate and concentrated. The residue is triturated with diethyl ether, filtered off with suction and dried.

Yield: 1.28 g (crude product).

70d. (2-((R,S)-4-(4-(aminoiminomethyl)phenyl)-4-methyl-2,5-dioxoimidazolidin-1-yl)acetyl-L-aspartyl-(1-adamantylmethyl)amide 1.28 g of (2-((R,S)-4-(4-(aminoiminomethyl) phenyl)-4-methyl-2,5-dioxoimidazolidin-1-yl)acetyl)-L-aspartyl-$C_\beta$-tert-butyl ester-(1-adamantylmethyl)amide hydrochloride are dissolved in a mixture of 11.52 ml of trifluoroacetic acid, 1.28 ml of water and 1.28 ml of dimercaptoethane. After 1 hour at room temperature, the mixture is concentrated under a water suction vacuum. The residue is triturated with diethyl ether, filtered off with suction and dried. For purification, the substance is chromatographed on Sephadex LH20 in a mixture consisting of glacial acetic acid, n-butanol and water. The fractions containing the pure substance are concentrated. The residue is dissolved in water in the presence of a little acetic acid and freeze-dried.

Yield: 841.1 mg; FAB MS $(M+H)^+=553$.

Example 71

Ethyl (S)-3-(((R,S)-4-(4-(aminoiminomethyl) phenyl)-4-methyl-2,5-dioxoimidazolidin-1-yl) acetylamino)-3-phenylpropionate hydrochloride 71a. (R)-2-Amino-2-phenylethanol 20 g (920 mmol) of lithium borohydride are dissolved in 420 ml of absolute tetrahydrofuran. 233.5 ml (1.84 mol) of trimethylchlorosilane are added dropwise, while stirring, and 69.5 g (0.46 mol) of (R)-phenylglycine are then added in portions within the space of 4 hours. The reaction mixture is stirred at room temperature overnight. 690 ml of methanol are then added and the mixture is stirred at room temperature for 2 hours and concentrated in vacuo. The residue is dissolved, while stirring, in 690 ml of a 20% aqueous solution of potassium hydroxide. The aqueous phase is extracted three times with ethyl acetate. The combined organic phases are washed with water, dried over magnesium sulphate and concentrated in vacuo.

Yield: 41.2 g (65.3%); FAB MS $(M+H)^+=138$.

71b. (R)-2-Benzyloxycarbonylamino-2-phenylethanol 40.5 g (295 mmol) of (R)-2-amino-2-phenylethanol are dissolved in 385 ml of absolute dimethylformamide. 73.5 g of N-(benzyloxycarbonyloxy)succinimide (295 mmol) are added, at 0° C. and while stirring, and the mixture is then stirred at 0° C. for 1 hour. The ice bath is removed and the mixture is left to stand at room temperature for 48 h. The reaction solution is concentrated in vacuo and the residue is then taken up in 500 ml of ethyl acetate. The organic phase is washed twice with a 10% aqueous solution of citric acid and once with water. It is then dried over anhydrous sodium sulphate and concentrated. The resulting crystalline crude product (82.3 g) is once again dissolved in ethyl acetate. The organic phase is washed twice with a 10% aqueous solution of citric acid and once with water. Recrystallization subsequently takes place from ethyl acetate/petroleum ether.

Yield: 74.6 g (93.3%); FAB MS $(M+H)^+=272$.

71c. ((R)-2-Benzyloxycarbonylamino-2-phenylethyl)-4-methylphenyl-sulphonate 53.9 g of (R)-2-benzyloxycarbonylamino-2-phenylethanol (198.7 mmol) are dissolved in a mixture consisting of 500 ml of methylene chloride and 80.3 ml (993.5 mmol) of pyridine. 45.5 g (238.4 mmol) of tosyl chloride in 240 ml of methylene chloride are added, at 0° C.

and while stirring, and the mixture is left to stir at room temperature for 7 hours. A further 11.36 g of tosyl chloride (59.61 mmol) are added. The mixture is left to stir at 0° C. for 5 hours. The mixture is then left to stand at room temperature overnight and concentrated in vacuo. The residue is taken up in ethyl acetate. The organic phase is washed three times with a 10% aqueous solution of citric acid and twice with water, dried over magnesium sulphate and concentrated in vacuo. The residue is triturated with diethyl ether, filtered off with suction, washed with diethyl ether and dried over phosphorus pentoxide. Yield: 60.9 g (72%). The mother liquor is concentrated, taken up in n-heptane/ethyl acetate (6:4) and chromatographed on silica gel. Yield: 3.5 g (4.2%).

Total yield: 64.4 g (76.2%); FAB MS (M+H)$^+$=426.

71d. (S)-3-Benzyloxycarbonylamino-3-phenylpropionitrile 60.5 g of ((R)-2-benzyloxycarbonylamino-2-phenylethyl)-4-methylphenylsulphonate (142.2 mmol) are dissolved in 675 ml of dimethylformamide. 13.9 g of potassium cyanide (213.3 mmol), 5.64 g of 18-crown-6 (21.33 mmol) and 520 mg of potassium iodide (3.13 mmol) are added and the mixture is stirred at 50° C. for 20 hours. The reaction solution is poured into 500 ml of ice water and this mixture is subsequently stirred at 0° C. for 5 hours. The mixture is filtered with suction and the precipitate is dissolved in ethyl acetate. The organic phase is washed three times with water, dried over magnesium sulphate and concentrated in vacuo. The residue is triturated with diethyl ether, filtered off with suction, washed with diethyl ether and dried over phosphorus pentoxide.

Yield: 25.3 g (63.5%); FAB MS (M+H)$^+$=281.

71e. Ethyl (S)-3-benzyloxycarbonylamino-3-phenylpropionate 15 g of (S)-3-benzyloxycarbonylamino-3-phenylpropionitrile (53.51 mmol) are suspended in a mixture consisting of 110 ml of absolute ethanol and 30 ml of dioxane. HCl gas is passed in, while stirring and cooling, at 10–15° C. After a short time a clear solution is formed. Further HCl gas is passed in, while cooling, until starting material can no longer be detected in a thin layer chromatogram. Nitrogen is then passed through the reaction solution for 15 minutes and the mixture is subsequently concentrated in vacuo. Water is added to the residue until a lasting turbidity is obtained. The mixture is stirred at room temperature for 30 minutes and the aqueous phase is then extracted three times with ethyl acetate. The combined organic phases are washed with water, dried over magnesium sulphate and concentrated in vacuo. The residue is taken up in ethyl acetate/petroleum ether (1:1) and chromatographed on silica gel.

Yield: 10.55 g (60%); FAB MS (M+H)$^+$=328.

71f. Ethyl (S)-3-amino-3-phenylpropionate hydrochloride 10.29 g of ethyl (S)-3-benzyloxycarbonylamino-3-phenylpropionate (31.44 mmol) are dissolved in 125 ml of ethanol and hydrogenated catalytically over Pd/active charcoal at a Ph of 4 using an automated burette and while adding 2N ethanolic HCl. The catalyst is filtered off with suction through kieselguhr and the filtrate is concentrated. The residue is triturated with diethyl ether, filtered off with suction, washed with diethyl ether and dried over phosphorus pentoxide.

Yield: 5.05 g (70%); FAB MS (M+H)$^+$=194.

71g Ethyl (S)-3-(((R,S)-4-(4-(aminoiminomethyl)phenyl)-4-methyl-2,5-dioxoimidazolidin-1-yl)acetylamino)-3-phenylpropionate hydrochloride 10.4 ml of N-ethylmorpholine (80 mmol) and 17.6 g of DCC (80 mmol) are added, at 0° C., to a solution of 26.14 g of ((R,S)-4-(4-(aminoiminomethyl)phenyl-4-methyl-2,5-dioxoimidazolidin-1-yl)acetic acid hydrochloride (80 mmol) (Example 1), 18.37 g of ethyl (S)-3-amino-3-phenylpropionate hydrochloride (80 mmol) and 10.8 g of HOBt in 400 ml of dimethylformamide. The mixture is left to stir at 0° C. for 1 hour and at room temperature for 3 hours. The mixture is subsequently left to stand overnight and the precipitate is then filtered off with suction and the filtrate is concentrated. For purification, the oily residue (89 g) is chromatographed on Sephadex LH20 in a mixture consisting of glacial acetic acid, N-butanol and water. The fractions containing the pure substance are concentrated. The residue is dissolved in water and freeze-dried.

Yield: 35 g (94%); FAB MS (M+H)$^+$=466.

We claim:

1. 5-membered ring heterocycle of the formula:

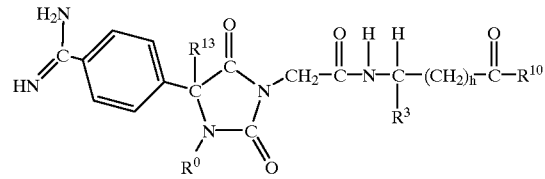

in which $R^0$ denotes hydrogen, $(C_1-C_8)$-alkyl, $(C_3-C_8)$-cycloalkyl, substituted or unsubstituted $(C_6-C_{14})$-aryl, or $(C_6-C_{14})$-aryl-$(C_1-C_8)$-alkyl which is substituted or unsubstituted in the aryl radical;

$R^3$ denotes hydrogen, $(C_1-C_8)$-alkyl, substituted or unsubstituted $(C_6-C_{14})$-aryl or CONHR$^{14}$;

$R^{10}$ denotes hydroxyl or $(C_1-C_4)$-alkoxyl;

$R^{13}$ denotes $(C_1-C_6)$-alkyl, $(C_6-C_{14})$-aryl-$(C_1-C_8)$-alkyl which is substituted or unsubstituted in the aryl radical, or $(C_3-C_8)$-cycloalkyl;

$R^{14}$ denotes $(C_1-C_6)$-alkyl which is substituted by hydroxycarbonyl or $(C_1-C_4)$-alkoxycarbonyl and, optionally, by a phenyl radical;

and h represents 1 or 2, or the physiologically tolerated salts thereof.

2. 5-Membered ring heterocycle according to claim 1 in which $R^{13}$ represents $(C_1-C_6)$-alkyl, $(C_3-C_7)$-cycloalkyl or benzyl.

3. 5-Membered ring heterocycle according to claim 2 in which $R^{13}$ represents methyl.

4. 5-Membered ring heterocycle according to claim 1 in which, at the same time, $R^0$ represents hydrogen;

$R^3$ represents phenyl;

$R^{10}$ represents hydroxy, methoxy, ethoxy or isopropoxy; and $R^{13}$ represents methyl;

h represents 1.

5. 5-Membered ring heterocycle according to claim 1 in which $R^{10}$ represents hydroxy and in which the chiral center in the 4-position of the imidazolidine ring is present in the S configuration and the chiral carbon atom to which $R^3$ is attached is present in the S configuration, or the physiologically tolerated salts thereof.

6. 5-Membered ring heterocycle according to claim 1 in which $R^{10}$ represents hydroxy and in which the chiral center in the 4-position of the imidazolidine ring is present in the R configuration and the chiral carbon atom to which $R^3$ is attached is present in the S configuration or the physiologically tolerated salts thereof.

7. 5-Membered ring heterocycle according to claim 1 in which $R^{10}$ represents ethoxy and in which the chiral center in the 4-position of the imidazolidine ring is present in the S configuration and the chiral carbon atom to which $R^3$ is attached is present in the S configuration, or the physiologically tolerated salts thereof.

8. 5-Membered ring heterocycle according to claim 1 in which $R^{10}$ represents ethoxy and in which the chiral center in the 4-position of the imidazolidine ring is present in the R configuration and the chiral carbon atom to which $R^3$ is attached is present in the S configuration, or the physiologically tolerated salts thereof.

9. 5-Membered ring heterocycle according to claim 1 in which $R^0$ denotes benzyl which is substituted or unsubstituted in the phenyl radical.

10. ((R,S)-4-(4-(Amino-imino-methyl)phenyl)-4-methyl-2,5-dioxoimidazolidin-1-yl)-acetyl-L-aspartyl-L-phenylglycine, or a physiologically tolerated salt thereof.

11. ((R)-4-(4-(Amino-imino-methyl)phenyl)-4-methyl-2,5-dioxoimidazolidin-1-yl)-acetyl-L-aspartyl-L-phenylglycine, or a physiologically tolerated salt thereof.

12. ((S)-4-(4-(Amino-imino-methyl)phenyl)-4-methyl-2,5-dioxoimidazolidin-1-yl)-acetyl-L-aspartyl-L-phenylglycine, or a physiologically tolerated salt thereof.

13. ((R,S)-4-(4-(Amino-imino-methyl)phenyl)-4-cyclopropyl-2,5-dioxoimidazolidin-1-yl)acetyl-L-aspartyl-L-phenylglycine, or a physiologically tolerated salt thereof.

14. ((R,S)-4-(4-(Amino-imino-methyl)phenyl)-4-ethyl-2,5-dioxoimidazolidin-1-yl)-acetyl-L-aspartyl-L-phenylglycine, or a physiologically tolerated salt thereof.

15. ((R,S)-4-(4-(Amino-imino-methyl)phenyl)-4-benzyl-2,5-dioxoimidazolidin-1-yl)-acetyl-L-aspartyl-L-phenylglycine, or a physiologically tolerated salt thereof.

16. ((R,S)-4-(4-(Amino-imino-methyl)phenyl)-4-tert-butyl-2,5-dioxoimidazolidin-1-yl)-acetyl-L-aspartyl-L-phenylglycine, or a physiologically tolerated salt thereof.

17. (S)-3-(((R,S)-4-(4-(Amino-imino-methyl)phenyl)-4-methyl-2,5-dioxoimidazolidin-1-yl)-acetyl-L-acetylamino)-3-phenylpropionic acid, or a physiologically tolerated salt thereof.

18. (S)-3-(((S)-4-(4-(Amino-imino-methyl)phenyl)-4-methyl-2,5-dioxoimidazolidin-1-yl)acetylamino)-3-phenylpropionic acid, or a physiologically tolerated salt thereof.

19. Process for preparing a compound according to claim 1 characterized by the condensation of a compound of the formula:

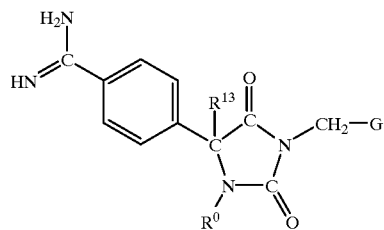

with a compound of the formula:

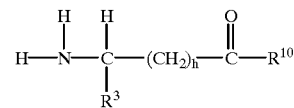

in which $R^0$, $R^3$, $R^{10}$, $R^{13}$ and h are defined as indicated in claim 1, and G represents hydroxycarbonyl, $(C_1-C_6)$-alkoxycarbonyl, carboxylic acid chlorides, esters or anhydrides, or represents isocyanato.

20. Process for the treatment of a host in need thereof comprising administering an effective dose of a compound according to claim 1 or of its physiologically tolerated salts, as inhibitors of thrombocyte aggregation, of the metastasization of carcinoma cells, of the binding of osteoclasts to the bone surface, or for the treatment of thromboses.

21. Pharmaceutical preparation, characterized in that it contains one or more compounds according to claim 1 or one or more physiologically tolerated salts thereof, as active compound together with pharmaceutically acceptable excipients and additives.

22. Process for producing a pharmaceutical preparation, containing one or more compounds according to claim 1, or one or more physiologically tolerated salts thereof, characterized by mixing them together with pharmaceutically acceptable excipients and additives to produce a preparation suitable for administration.

23. Ethyl (S)-3-(((R,S)-4-(4-amino-imino-methyl)phenyl)-4-methyl-2,5-dioxoimidazolidin-1-yl)acetylamino)-3-phenylpropionate, or a physiologically tolerated salt thereof.

24. Ethyl (S)-3-(((S)-4-(4-amino-imino-methyl)phenyl)-4-methyl-2,5-dioxoimidazolidin-1-yl)acetylamino)-3-phenylpropionate, or a physiologically tolerated salt thereof.

25. Methyl (S)-3-(((S)-4-(4-amino-imino-methyl)phenyl)-4-methyl-2,5-dioxoimidazolidin-1-yl)acetylamino)-3-phenylpropionate, or a physiologically tolerated salt thereof.

26. Isopropyl (S)-3-(((S)-4-(4-amino-imino-methyl)phenyl)-4-methyl-2,5-dioxoimidazolidin-1-yl)acetylamino)-3-phenylpropionate, or a physiologically tolerated salt thereof.

27. ((R,S)-4-(4-Amino-imino-methyl)phenyl)-4-methyl-2,5-dioxoimidazolidin-1-yl)acetyl-L-aspartyl-L-phenlglycine dimethyl ester, or a physiologically tolerated salt thereof.

28. ((R,S)-4-(4-Amino-imino-methyl)phenyl)-4-methyl-2,5-dioxoimidazolidin-1-yl)acetyl-L-aspartyl-L-phenlglycine diisopropyl ester, or a physiologically tolerated salt thereof.

29. ((R,S)-4-(4-Amino-imino-methyl)phenyl)-4-methyl-2,5-dioxoimidazolidin-1-yl)acetyl-L-aspartyl-L-phenlglycine methyl ester, or a physiologically tolerated salt thereof.

* * * * *